United States Patent
Woolley et al.

(10) Patent No.: US 8,101,037 B1
(45) Date of Patent: Jan. 24, 2012

(54) PHASE-CHANGING SACRIFICIAL MATERIALS FOR MANUFACTURE OF HIGH-PERFORMANCE POLYMERIC CAPILLARY MICROCHIPS

(76) Inventors: Adam T. Woolley, Orem, UT (US);
Ryan T. Kelly, West Richland, WA (US);
Melissa Draper Fisk, Provo, UT (US)

(*) Notice: Subject to any disclaimer, the term of this patent is extended or adjusted under 35 U.S.C. 154(b) by 84 days.

(21) Appl. No.: 12/724,404

(22) Filed: Mar. 15, 2010

Related U.S. Application Data

(62) Division of application No. 11/346,398, filed on Feb. 1, 2006, now Pat. No. 7,686,907.

(60) Provisional application No. 60/649,325, filed on Feb. 1, 2005.

(51) Int. Cl.
| | |
|---|---|
| B32B 17/00 | (2006.01) |
| B32B 17/10 | (2006.01) |
| C03C 27/00 | (2006.01) |
| C03C 15/00 | (2006.01) |
| C03C 25/68 | (2006.01) |
| G02C 7/00 | (2006.01) |
| B29C 53/82 | (2006.01) |
| G01N 21/00 | (2006.01) |
| G01N 31/22 | (2006.01) |
| G01N 33/00 | (2006.01) |
| G01N 15/06 | (2006.01) |

(52) U.S. Cl. .......... 156/155; 156/99; 156/292; 204/601; 422/68.1; 216/36

(58) Field of Classification Search .............. 156/99, 156/101, 103, 105, 155, 272.2, 275.5, 292, 156/307.1; 204/451, 452, 601, 602; 422/58, 422/68.1, 82.05, 82.09, 100, 101, 102, 103, 422/104; 216/33, 36, 94, 95, 96, 97, 99, 216/100
See application file for complete search history.

(56) References Cited

U.S. PATENT DOCUMENTS

| | | | |
|---|---|---|---|
| 3,534,757 A | 10/1970 | Doherty | |
| 3,676,238 A * | 7/1972 | Furlong et al. | 156/242 |
| 5,804,280 A | 9/1998 | Pall | |
| 6,599,436 B1 | 7/2003 | Matzke | |
| 2003/0029723 A1 | 2/2003 | Yu | |
| 2004/0144647 A1* | 7/2004 | Dorner et al. | 204/450 |
| 2005/0277125 A1 | 12/2005 | Benn et al. | |
| 2006/0078470 A1* | 4/2006 | Zhou et al. | 422/100 |

FOREIGN PATENT DOCUMENTS

| | | |
|---|---|---|
| WO | WO2005/084191 | 9/2005 |
| WO | WO 2005084191 A2 * | 9/2005 |

OTHER PUBLICATIONS

Demello, 2 Lab Chip 31N (2002).
Becker, 56 Talanta 267 (2002).
Boone, 74 Anal. Chem. 78A (2002).
Reyes, 74 Anal. Chem. 2623 (2002).
Martynova, 69 Anal. Chem. 4783 (1997).

(Continued)

*Primary Examiner* — Philip Tucker
*Assistant Examiner* — Brian R Slawski
(74) *Attorney, Agent, or Firm* — James Sonntag

(57) ABSTRACT

A microchip with capillaries and method for making same is described. A sacrificial material fills microchannels formed in a polymeric substrate, the filled microchannels are covered by a top cover to form filed capillaries, and the sacrificial material is removed to form the microcapillaries. The sacrificial material fills the microchannels as a liquid whereupon it becomes solid in the microchannels, and is liquefied after the top cover is applied and affixed to remove the sacrificial material. The top cover may be solvent sealed on the substrate and of the same or different material as the substrate. The top cover may also be an in situ applied semipermeable membrane.

18 Claims, 26 Drawing Sheets

OTHER PUBLICATIONS

Duffy, 70 Anal. Chem. 4974 (1998).
Jacobson, 70 Anal. Chem. 3476 (1998).
Culbertson, 72 Anal. Chem. 5814 (2000).
Paegle, 99 Anal. Chem. 574 (2002).pdf.
Becker, 21 Electrophoresis 12 (2000).
Soper, 72 Anal. Chem. 643A (2000).
Wang, Sens. Actuators B 199 (1997).
Chiem, 63 Sens. Actuators B 146 (2000).
Ito, 81 Sens. Actuators 187 (2002).
Jia, 76 Anal. Chem. 5597 (2004).
Turner, 16 J Vac. Sci. Tech. B 3835 (1998).
Foquet, 74 Anal. Chem. 1415 (2002).
Suh, 9 J Microelectromechanical Sys 198 (2000).
Harnett, 19 J. Vac. Sci. Tech. 2842 (2001).
Jayachandran, 12 J Microelectromechanical Sys 147 (2003).
Metz, 4 Lab Chip 114 (2004).
Sethu, 104 Sesnors and Actuators a 283 (2003).
Klintbert, 103 Sensors and Actuators A 307 (2003).
Liu, 76 Anal. Chem. 1824 (2004).
Pal, 76 Anal. Chem. 3740 (2004).
Rocklin, 72 Anal. Chem. 5244 (2000).
Gottschlich, 73 Anal. Chem. 2669 (2001).
Ramsey, 75 Anal. Chem. 3758 (2003).
Dou, 23 Electrophoresis 3558 (2002).
Lacher, 1004 J Chromo a 225 (2003).
Hu, 24 Electrophoresis 3679 (2003).
Kato, 76 Anal. Chem 6792 (2004).
Harrison, 64 Anal. Chem. 1926 (1992).
Monnig, 63 Anal. Chem. 802 (1991).
Shen, 71 Anal. Chem 5348 (1999).
Shen, J Microcolumn Separations 135 (2000).
Manz, B1 Sensors & Actuators 244 (1990).
Lee, 75 Anal. Chem 6544 (2003).
Buckholtz, 23 Electrophoresis 1398 (2002).
Pumera, 74 Anal. CHem 1968 (2002).
Landers, 75 Anal. Chem. 2919 (2003).
Dolnik, 21 Anal. Chem. 41 (2000).
Kelly, 77 Anal.
Taghavi-Moghadam, 5 Org. Proc. Res. & Dev. 652 (2001).
Terry, 26 IEEE Trans Elect Devices 1880 (1979).
Kelly, 75 Anal. Chem. 1941 (2003).
Monnig, 63 Anal. Chem. 802 (1991).
Galloway, 74 Anal. Chem. 2407 (2002).
Ford, 121 J Biomech Eng 13 (1999).
Kelly, 75 Anal. Chem. 1941 (2003).
Mccormick, 69 Anal.Chem 2626 (p. In list are incorrect) (1997).
Song, 20 Electrophoresis 2847 (1999).
Xu, 72 Anal. Chem. 1930 (2000).
Kelly, 77 Anal. Chem. 3536 (2005).
Myers, 1044 J. Chromogr. 253 (2004).
Liu, 73 Anal. Chem. 4196 (2001).
Humble, 76 Anal. Chem. 5641 (2004).
PEG Webpage.
Wang, 985 J. Chromatogr. 455 (2003).
Huang, 71 Anal. Chem. 1628 (1999).
Greenlee, 14 Biotechnol.
Koegler, 12 Biotechnol. Prog. 822 (1996).
Song, 76 Anal. Chem. 2367 (2004).
Shen, 71 Anal. Chem. 5348 (1999).pdf.
Zhang, 128 Analyst 537 (2003).
Reichardt, webpage—Reichardt, Properties and Toxicities of Organic Solvents.
Jacobson, 70 Anal. Chem. 3476 (1998).
Culbertson, 72 Anal. Chem. 5814 (2000).
Emrich, 74 Anal. Chem. 5076 (2002).
Khandurina, 72 Anal. Chem. 2995 (2000).
Liu, 128 Analyst 1002 (2003).
Vilkner, 76 Anal. Chem. 3373 (2004).
Erickson, 507 Anal. Chim. Acta 11 (2004).
Lagally, 37 J. Phys. D. R245 (2004).
Cheng, 73 Anal. Chem. 1472 (2001).pdf.
Ramchandani, 76 Anal. Chem. 3162 (2004).
Xiang, 71 Anal. Chem. 1485 (1999).
Jiang, 73 Anal. Chem. 2048 (2001).
Kuo, 75 Anal. Chem. 1861 (2003).
Cannon, 75 Anal. Chem. 2224 (2003).
Kuo, 102 Sens. Acutators A 223 (2003).
Khandurina, 71 Anal. Chem. 1815 (1999).

* cited by examiner

PHASE-CHANGING SACRIFICIAL MATERIALS FOR MANUFACTURE OF HIGH-PERFORMANCE POLYMERIC CAPILLARY MICROCHIPS

CROSS REFERENCE TO RELATED APPLICATIONS

This application is a divisional from U.S. patent application Ser. No. 11/346,398, filed 1 Feb. 2006 now U.S. Pat. No. 7,686,907, which claims priority from U.S. Provisional Patent Application 60/649,325, filed 1 Feb. 2005.

FEDERAL RESEARCH STATEMENT

This invention was made with support from United States Government, and the United States Government has certain rights in this invention pursuant to contract number R01 GM064547-01 A1, National Institutes of Health.

BACKGROUND OF INVENTION

Although a relatively new area of study, micromachined chemical analysis systems have the potential to revolutionize separation methods, much like integrated circuit manufacturing transformed advanced computation in the twentieth century. Miniaturized devices promise to reduce both reagent consumption and cost while simultaneously increasing separation speed and throughput. Already, microdevices have been utilized in clinical diagnostics[41], analytical chemistry[42], human genome research[43], and in the pharmaceutical industry,[44] allowing new access to information on the molecular level.

Miniaturization in chemical separations had its start in the late 1970's when Terry et al.[45] microfabricated an integrated gas chromatography system on a silicon wafer. While this initial work went largely unnoticed for more than a decade, efforts in this area were renewed in the 1990's with the publication of a conceptual miniaturized total chemical analysis system in 1990[46] and the development of planar microfabricated capillary electrophoresis (CE) substrates in 1992.[47] These studies sparked an increasing interest in miniaturization, creating a demand for devices with ever-improving functionality at ever-lower costs.

The use of polymeric microchip substrates has been an important advance. Currently, glass devices predominate for a number of reasons. First, the chemistry of glass surfaces is well understood. Second, glass is transparent to visible light wavelengths and has low intrinsic fluorescence,[48] a critical characteristic, since detection often involves monitoring of optical signals, such as fluorescence, UV absorbance, or Raman scattering. Finally, photolithographic processes already used for silicon materials can be readily adapted to glass substrates. Despite these advantages, there are also several significant drawbacks to working with glass. For example, substrate costs for glass can exceed those for common polymers by a factor of 10 to 100 (see Table 1). Expenses also accumulate during the many steps involved in preparing glass substrates, such as cleaning, photoresist coating, photolithography, development, etching, etc., making the fabrication process not only pricey, but also complicated and time consuming. Furthermore, microcapillary formation in glass materials requires a high-temperature (>600° C.) annealing step. Finally, once a substrate is fully prepared, a surface modification procedure is often necessary because many biomolecules can adsorb to native glass.

TABLE 1

Prices for polymers and different types of glass.[49, 50]

| Material | Cents per cm$^2$ |
| --- | --- |
| Poly(methyl methacrylate) (PMMA) | 0.2-2 |
| Polycarbonate (PC) | 0.5-4 |
| Borofloat glass | 10-20 |
| Borosilicate glass | 5-15 |
| Photostructurable glass | 20-40 |

Research into replacing glass in microdevices with polymers began in the mid-1990's. An all-plastic microfluidic system was reported in 1996 by VerLee et al.,[51] however, the channel dimensions were still in the range of conventional fused silica capillary diameters (~100 μm). Shortly thereafter researchers began to develop smaller (15-20 μm) plastic microchannels.[52] Because plastics are typically less expensive, more biocompatible, and easier to manipulate than silica- or silicon-based materials, the development of suitable polymer microfabrication methods continues to be important for the production of low-cost, disposable miniaturized devices.

As the lab-on-a-chip field has developed, certain polymers such as poly(dimethylsiloxane) (PDMS), poly(methyl methacrylate) (PMMA) and polycarbonate (PC) have been employed increasingly as device substrates.[1-3] This shift toward polymeric substrates has likely occurred because of two factors. First, the templated procedures used to create microchips in polymers allow a single photolithographically defined master to be used to pattern numerous devices,[5,6] thus decreasing the need for cleanrooms and other costly instrumentation. Second, the polymeric materials themselves are typically less expensive than microchip-quality glass, and lower costs per device should facilitate the development of disposable microfluidic systems.[3]

Despite these attractive features of polymeric materials, glass remains the substrate of choice for very fast[7] or high-performance[8,9] microchip CE. This performance gap is due in part to the convenience of adapting the well-characterized chemistry of fused silica capillaries for surface modification in a wide array of glass microchip applications. Also, the thermal conductivity of glass is higher than that of commonly used polymers (e.g. PMMA, PC and PDMS),[10] which provides better dissipation of Joule heating and enables higher electric fields in microchannels in glass substrates.

Unfortunately, glass microchips must be patterned and etched individually in a cleanroom, and the thermal annealing of glass substrates to enclose microcapillaries generally takes place in a furnace at >400° C. for several hours.[1] Moreover, special care must be taken to ensure that the bonded surfaces are extremely clean and lacking even small particulates, or thermal bonding will not be successful.[11] Low- and room-temperature glass bonding approaches that avoid high-temperature processing have been reported,[12-15] but the resulting adhesion is weaker than in thermally sealed devices, and even greater care must be taken to ensure that the surfaces are extremely clean and flat.

To avoid a sealing step for microcapillary enclosure and to create sub-μm features, sacrificial techniques have been explored. In these methods a channel design is patterned on top of a bulk substrate, and a thin film of a different material is deposited over the entire surface, covering the patterned design. Next, the sacrificial material under the deposited layer is etched away[16,17] or thermally decomposed,[18-21] leaving microcapillaries defined by the cover layer and the base substrate. While these sacrificial methods have successfully created devices without a thermal bonding step, the fabrication protocols are involved, and templated procedures are not possible because each device is patterned individually.

Other approaches for microfluidic device construction involve the creation of capillaries by affixing a cover plate to a surface containing microfabricated channels. Several approaches for sealing polymer substrates have been utilized to form microcapillaries, including heating in a convection oven,[52,53] placement under heated weights[54] or in boiling water,[55] thermal lamination,[56] and adhesion with tape[57] or poly(dimethylsiloxane) (PDMS) films.[58] While adhesive tapes and elastomer films are convenient, thermal-bonding approaches continue to predominate because they enable the formation of microcapillaries with a uniform surface composed entirely of the same polymeric material. Since substances have characteristic surface charge distributions (or zeta potential), when a channel is comprised of different top and bottom materials, as is necessitated by adhesive and elastomer bonding, the different surface properties result in unwanted band broadening in separations. On the other hand, the temperatures necessary for thermal bonding, normally >100° C. for polymers, often result in undesired reactions of microchip surface coatings. Because of these limitations, the development of new bonding techniques remains an important focus of microchip fabrication research.

Phase-changing materials (typically waxes) have been incorporated into fluidic microchips to create micropumps,[22] membrane actuators[23] and valves,[24,25] but these materials have not been used as sacrificial layers in microdevice fabrication. In addition, Liu, et al.[24] recently used a solvent-assisted thermal bonding method to seal PC substrates at ~200° C., but the large feature dimensions (>300 µm deep) made it unnecessary to protect the channels from the bonding solvent.

Microfluidic devices have made possible extremely fast[72] and high-performance[73-75] chemical separations, but perhaps the most significant promise of lab-on-a-chip technology is in the ability to combine multiple sample handling and analysis steps onto a single miniaturized platform.[76-79] Such integration can decrease the total analysis time significantly, especially with complex samples that require extensive pretreatment. For example, microfluidic mixers and reactors have been combined on microchip capillary electrophoresis (µ-CE) devices having six parallel separation lanes to perform multiple immunoassays in ~1 min.[80] In another case µ-CE systems with polymerase chain reaction chambers having on-chip heaters, temperature sensors and valves facilitated genotyping from whole bacterial cells in <10 min.[81] However, one challenge associated with µ-CE is concentration sensitivity, since small sample volumes are loaded in these systems typically. Thus, it can be advantageous to integrate sample clean up and preconcentration on-chip to enhance the signal intensity from dilute specimens.

As size-selective membranes can facilitate many sample preparation and manipulation steps, researchers have focused on interfacing membranes with microfluidics. For example, Smith and coworkers[82] created a microdialysis system that sandwiched commercially available sheet membranes between microchannel-containing substrates, allowing samples to be purified from interfering high- and low-molecular weight species prior to being introduced into a mass spectrometer. In a similar setup affinity microdialysis was performed on-chip; antigen-antibody complexes were retained by a sheet membrane while smaller, unbound components were removed.[83] Then, the purified complexes were exposed to counterflowing air through a second membrane, which concentrated the sample through solution evaporation. Nanoporous track-etched polycarbonate membranes were utilized in interfacing microchannels on different substrates.[84-86] Analyte transport between channels was controlled by applying an electric field across the membrane, enabling selected fractions from one channel network to be driven electrokinetically through the nanopores and introduced into the opposing channel structure. Samples were injected and fractions were collected across a membrane using this approach, showing considerable control in analyte manipulation. Ramsey et al.[87,88] demonstrated size-selective barriers for DNA concentration prior to electrophoretic separation. Channels in a µ-CE injector were connected electrically through small pores in a thin sodium silicate layer. DNA molecules that were driven electrokinetically to the sodium silicate membrane were too large to pass through, and over time the concentration of the trapped DNA increased ~100-fold; the enriched sample plugs were then separated electrophoretically. Zhang and Timperman[89] employed a conceptually similar preconcentration system that had a sandwiched, track-etched membrane. Rather than pore size, charge played the dominant role in analyte trapping, as the 10-50 nm through holes were much larger than the molecules that were enriched. While these examples demonstrate the broad applicability of membrane-based microsystems to various modes of sample pretreatment and manipulation, most utilized commercial sheet membranes sandwiched between microfluidic device substrates. Such configurations have limited device geometries and are constrained by the properties of available materials.

The ability to polymerize semi-permeable barriers in situ in microfluidic networks adds design flexibility and enables membranes with a variety of properties to be explored. Recently, a dialysis system that incorporated an in situ-polymerized membrane was reported by Kirby and coworkers.[90] A microchannel was filled with a prepolymer solution having an appropriate photoinitiator, and a laser beam was focused into a plane to effect spatially controlled polymerization. This produced a membrane that divided the channel in two along its length, allowing dialysis to take place between counter-current flows. Membrane properties could be altered by tailoring the prepolymer composition, but a complicated optical setup was required, and repeated laser exposures with fresh monomer solution in the channels were necessary to complete polymerization. Thus, improved methods are still needed for the convenient creation of polymer membranes in microfluidic networks.

Electric field gradient focusing (EFGF) is an analytical technique that is facilitated by having a semi-permeable membrane interfaced with a separation column.[91-97] Briefly, a gradient in electric field, combined with a constant-velocity pressure-driven flow in the opposite direction, causes charged analytes to focus into stationary bands along the column according to electrophoretic mobility. A capillary-based EFGF design that interfaced an in situ-polymerized semi-permeable copolymer (SPC) of changing cross-sectional area (CSA) with a ~100 µm-diameter focusing column has been reported.[95] The SPC permitted current-carrying buffer ions to pass through, but the bulk fluid and protein analytes could not. The focusing column was formed by polymerizing the SPC around a wire in a well of changing CSA. After polymerization the wire was pulled out from one of the ends of the microchip, leaving an open cylindrical column connected to capillaries at both sides of the SPC. Although this approach allowed for smaller-dimension devices than previous membrane-incorporating EFGF designs,[91-93,97] several limitations were also apparent. For example, further column miniaturization was impractical, as thinner wires were more fragile and difficult to use. In addition, a diameter mismatch between the focusing channel and the capillaries would reduce resolution if analytes were eluted from the column. Improved EFGF device fabrication methods that avoid these challenges, while enabling smaller channel dimensions, would be valuable.

TABLE 2

REFERENCES 1. de Mello, A. J. Lab Chip 2002, 2, 31 N-36N.
2. Becker, H.; Locascio, L. E. Talanta 2002, 56, 267-287.
3. Boone, T. D.; Fan, Z. H.; Hooper, H. H.; Ricco, A. J.; Tan, H.; Williams, S. J. Anal. Chem. 2002, 74, 78A-86A.
4. Reyes, D. R.; Iossifidis, D.; Auroux, P.-A.; Manz, A. Anal. Chem. 2002, 74, 2623-2636.
5. Martynova, L.; Locascio, L. E.; Gaitan, M.; Kramer, G. W.; Christensen, R. G.; MacCrehan, W. A. Anal. Chem. 1997, 69, 4783-4789.
6. Duffy, D. C.; McDonald, J. C.; Schueller, O. J. A.; Whitesides, G. M. Anal. Chem. 1998, 70, 4974-4984.
7. Jacobson, S. C.; Culbertson, C. T.; Daler, J. E.; Ramsey, J. M. Anal. Chem. 1998, 70, 3476-3480.
8. Culbertson, C. T.; Jacobson, S. C.; Ramsey, J. M. Anal. Chem. 2000, 72, 5814-5819.
9. Paegel, B. M.; Emrich, C. A.; Wedemayer, G. J.; Scherer, J. R.; Mathies, R. A. Proc. Natl. Acad. Sci. USA 2002, 99, 574-579.
10. MatWeb Material Property Data. http://www.matweb.com (accessed Jan 2005).
11. Simpson, P. C.; Woolley, A. T.; Mathies, R. A. J. Biomed. Microdevices 1998, 1, 7-26.
12. Wang, H. Y.; Foote, R. S.; Jacobson, S. C.; Schneibel, J. H.; Ramsey, J. M. Sens. Actuators B 1997, 45, 199-207.
13. Chiem, N.; Lockyear-Shultz, L.; Andersson, P.; Skinner, C.; Harrison, D. J. Sens. Actuators B 2000, 63, 147-152.
14. Ito, T.; Sobue, K.; Ohya, S. Sens. Actuators B 2002, 81, 187-195.
15. Jia, Z.-J.; Fang, Q.; Fang, Z.-L. Anal. Chem. 2004, 76, 5597-5602.
16. Turner, S. W.; Perez, A. M.; Lopez, A.; Craighead, H. G. J. Vac. Sci. Technol. B 1998, 16, 3835-3840.
17. Foquet, M.; Korlach, J.; Zipfel, W.; Webb, W. W.; Craighead, H. G. Anal. Chem. 2002, 74, 1415-1422.
18. Suh, H.-J.; Bharathi, P.; Beebe, D. J.; Moore, J. S. J. Microelectromech. Syst. 2000, 9, 198-205.
19. Harnett, C. K.; Coates, G. W.; Craighead, H. G. J. Vac. Sci. Technol. B 2001, 19, 2842-2845.
20. Jayachandran, J. P.; Reed, H. A.; Zhen, H.; Rhodes, L. F.; Henderson, C. L.; Allen, S. A. B.; Kohl, P. A. J. Microelectromech. Syst. 2003, 12, 147-159.
21. Metz, S.; Jiguet, S.; Bertsch, A.; Renaud, P. Lab Chip 2004, 4, 114-120.
22. Sethu, P.; Mastrangelo, C. H. Sens. Actuators A 2003, 104, 283-289.
23. Klintberg, L.; Svedberg, M.; Nikolajeff, F.; Thornell, G. Sens. Actuators A 2003, 103, 307-316.
24. Liu, R. H.; Yang, J.; Lenigk, R.; Bonanno, J.; Grodzinski, P. Anal. Chem. 2004, 76, 1824-1831.
25. Pal, R.; Yang, M.; Johnson, B. N.; Burke, D. T.; Burns, M. A. Anal. Chem. 2004, 76, 3740-3748.
26. Rocklin, R. D.; Ramsey, R. S.; Ramsey, J. M. Anal. Chem. 2000, 72, 5244-5249.
27. Gottschlich, N.; Jacobson, S. C.; Culbertson, C. T.; Ramsey, J. M. Anal. Chem. 2001, 73, 2669-2674.
28. Ramsey, J. D.; Jacobson, S. C.; Culbertson, C. T.; Ramsey, J. M. Anal. Chem. 2003, 75, 3758-3764.
29. Dou, Y.-H.; Bao, N.; Xu, J.-J.; Chen, H.-Y. Electrophoresis 2002, 23, 3558-3566.
30. Lacher, N. A.; de Rooij, N. F.; Verpoorte, E.; Lunte, S. M. J. Chromatogr. A 2003, 1004, 225-235.
31. Hu, S.; Ren, X.; Bachman, M.; Sims, C. E.; Li, G. P.; Allbritton, N. Electrophoresis 2003, 24, 3679-3688.
32. Kato, M.; Gyoten, Y.; Sakai-Kato, K.; Nakajima, T.; Toyo'oka, T. Anal. Chem. 2004, 76, 6792-6796.
33. Kelly, R. T.; Woolley, A. T. Anal. Chem. 2003, 75, 1941-1945.
34. Monnig, C. A.; Jorgenson, J. W. Anal. Chem. 1991, 63, 802-807.
35. Shen, Y.; Xiang, F.; Veenstra, T. D.; Fung, E. N.; Smith, R. D. Anal. Chem. 1999, 71, 5348-5353.
36. Shen, Y.; Smith, R. D. J. Microcolumn Sep. 2000, 12, 135-141.
37. Sanders, J. C.; Breadmore, M. C.; Kwok, Y. C.; Horsman, K. M.; Landers, J. P. Anal. Chem. 2003, 75, 986-994.
38. Lee, J. N.; Park, C.; Whitesides, G. M. Anal. Chem. 2003, 75, 6544-6554.
39. Buchholz, B. A.; Shi, W.; Barron, A. E. Electrophoresis 2002, 23, 1398-1409.
40. Pumera, M.; Wang, J.; Opekar, F.; Jelinek, I.; Feldman, J.; Lowe, H.; Hardt, S. Anal. Chem. 2002, 74, 1968-1971.
41. Landers, J. P. Anal. Chem. 2003, 57, 2919-2927.
42. Dolnik, V.; Liu, S.; Jovanovich, S. Electrophoresis 2000, 21, 41-54.
43. Kelly, R. T.; Woolley, A. T. Anal. Chem. 2005, 77, 96A-102A.
44. Taghavi-Moghadam, S.; Kleeman, A.; Golbig, K. G. Org. Proc. Res. Dev. 2001, 5, 652-658.
45. Terry, S. C.; Jermann, J. H.; Angell, J. B. IEEE Trans. Electron. Devices 1979, 26, 1880-1886.
46. Manz, A.; Graber, N.; Widmer, H. M. Sensors Actuators 1990, B 1, 244-248.
47. Harrison, D. J.; Manz, A.; Fan, Z. Anal. Chem. 1992, 64, 1926-1932.
48. Soper, S. A.; Ford, S. M.; Qi, S.; McCarley, R. L.; Kelly, K.; Murphy, M. C. Anal. Chem. 2000, 72, 643-651.
49. Modern Plastics website, www.modernplastics.com, accessed Oct. 30, 2004.
50. Becker, H.; Gartner, C. Electrophoresis 2000, 21, 12-26.

TABLE 2-continued

REFERENCES

51. Verlee, D.; Alcock, A.; Clark, G.; Huang, T. M.; Kantor, S.; Nemcek, T.; Norlie, J.; Pan, J.; Walsworth, F.; Wong, S.T. Proc. Solid State Sensor Actuator Workshop, Hilton Head, 1996, 9-14.
52. Martynova, L.; Locascio, L.E.; Gaitan, M.; Kanner, G. W.; Christensen, R. G.; MacCrehan, W. A. Anal. Chem. 1997, 9, 2626-2630.
53. Galloway, M.; Stryjewski, W.; Henry, A.; Ford, S. M.; Llopis, S.; McCarley, R. L.; Soper, S. A. Anal. Chem. 2002, 74, 2407-2415.
54. Ford, S. M.; Davies, J., Kar, B.; Qi, S. D.; McWhorter, S.; Soper, S. A.; Malek, C.K. J. Biomech. Eng. 1999, 121, 13-21.
55. Kelly, R. T.; Woolley, A. T. Anal. Chem. 2003, 75, 1941-1945.
56. McCormick, R. M.; Nelson, R. J.; Alonso-Amigo, M.G.; Benvegnu, D. J.; Hooper, H. H. Anal. Chem. 1997, 69, 4783-4789.
57. Song, L. G.; Fang, D. F.; Kobos, R. K.; Pace, S. J.; Chu, B. Electrophoresis 1999, 20, 2847-2855.
58. Xu, J. D.; Locascio, L.; Gaitan, M.; Lee, C. S. Anal. Chem. 2000, 72, 1930-1933.
59. Harper, C. A.; Petrie, E. M.; Plastics Materials and Processes: A Concise Encyclopedia, Wiley Interscience, 2003.
60. Kelly, R. T.; Pan, T.; Woolley, A. T. Anal. Chem. 2005, 77, 3536-3541.
61. Liu, Y.; Ganser, D.; Schneider, A.; Liu, R.; Grodzinski, P.; Kroutchinina, N. Anal. Chem. 2001, 73, 4196-4201.
62. Dupont, Comparison of PET, PETg, PETf Webpage, http://www.dupontteijinfilms.com/datasheets/petgpetf.html, accessed May 27, 2005.
63. PEG webpage, http://www.jtbaker.com/msds/englishhtml/p5029.htm, accessed May 27, 2005.
64. Crisco Homepage, www.crisco.com, accessed May 20, 2005.
65. S & J Lipids Webpage, Physical Properties of Even Chain Fatty Acids, http://www.sjlipids.com/fattyacd.htm, accessed Oct. 30, 2004.
66. California Institute of Technology, Overview About Waxes and Asphaltines, http://www.peer.caltech.edu/projects/1, accessed Oct. 30, 2004.
67. Yaley Enterprises Homepage, http://www.yaley.com, accessed May 20, 2005.
68. Chemical Resistance Chart, http://www.palram.com, accessed May 20, 2005.
69. Shen, Y.; Xiang, F.; Veenstra, T. D.; Fung, E. N.; Smith, R. D. Anal. Chem. 1999, 71, 5348-5353.
70. Michler, G. H. J. Mater. Sci. 1990, 25, 2321-2334.
71. Properties and Toxicities of Organic Solvents, from Christian Reichardt, Solvents and Solvent Effects in Organic Chemistry, VCH Publishers, 2nd ed., 1988, http://virtual.yosemite.cc.ca.us/smurov/orgsoltab.htm, accessed May 20, 2005.
72. Jacobson, S. C.; Culbertson, C. T.; Daler, J. E.; Ramsey, J. M. Anal. Chem. 1998, 70, 3476-3480.
73. Culbertson, C. T.; Jacobson, S. C.; Ramsey, J. M. Anal. Chem. 2000, 72, 5814-5819.
74. Emrich, C. A.; Tian, H.; Medintz, I. L.; Mathies, R. A. Anal. Chem. 2002, 74, 5076-5083.
75. Paegel, B. M.; Emrich, C. A.; Wedemayer, G. J.; Scherer, J. R.; Mathies, R. A. Proc. Natl. Acad. Sci. USA 2002, 99, 574-579.
76. Liu, Y.; Garcia, C. D.; Henry, C. S. Analyst 2003, 128, 1002-1008.
77. Vilkner, T.; Janasek, D.; Manz, A. Anal. Chem. 2004, 76, 3373-3386.
78. Erickson, D.; Li, D. Anal. Chim. Acta 2004, 507, 11-26.
79. Lagally, E. T.; Mathies, R. A. J. Phys. D 2004, 37, R245-R261.
80. Cheng, S. B.; Skinner, C. D.; Taylor, J.; Attiya, S.; Lee, W. E.; Picelli, G.; Harrison, D. J. Anal. Chem. 2001, 73, 1472-1479.
81. Lagally, E. T.; Scherer, J. R.; Blazej, R. G.; Toriello, N. M.; Diep, B. A.; Ramchandani, M.; Sensabaugh, G. F.; Riley, L. W.; Mathies, R. A. Anal. Chem. 2004, 76, 3162-3170.
82. Xiang, F.; Lin, Y.; Wen, J.; Matson, D. W.; Smith, R. D. Anal. Chem. 1999, 71, 1485-1490.
83. Jiang, Y.; Wang, P.-C.; Locascio, L. E.; Lee, C. S. Anal. Chem. 2001, 73, 2048-2053.
84. Kuo, T.-C.; Cannon, D. M., Jr.; Chen, Y. N.; Tulock, J. J.; Shannon, M. A.; Sweedler, J. V.; Bohn, P. W. Anal. Chem. 2003, 75, 1861-1867.
85. Cannon, D. M., Jr.; Kuo, T.-C.; Bohn, P. W.; Sweedler, J. V. Anal. Chem. 2003, 75, 2224-2230.
86. Kuo, T.-C.; Cannon, D. M., Jr.; Shannon, M. A.; Bohn, P. W.; Sweedler, J. V. Sens. Actuators A 2003, 102, 223-233.
87. Khandurina, J.; Jacobson, S. C.; Waters, L. C.; Foote, R. S.; Ramsey, J. M. Anal. Chem. 1999, 71, 1815-1819.
88. Khandurina, J.; McKnight, T. E.; Jacobson, S. C.; Waters, L. C.; Foote, R. S.; Ramsey, J. M. Anal. Chem. 2000, 72, 2995-3000.
89. Zhang, Y.; Timperman, A. T. Analyst 2003, 128, 537-542.
90. Song, S.; Singh, A. K.; Shepodd, T. J.; Kirby, B. J. Anal. Chem. 2004, 76, 2367-2373.
91. Koegler, W. S.; Ivory, C. F. Biotechnol. Prog. 1996, 12, 822-836.
92. Greenlee, R. D.; Ivory, C. F. Biotechnol. Prog. 1998, 14, 300-309.
93. Huang, Z.; Ivory, C. F. Anal. Chem. 1999, 71, 1628-1632.
94. Wang, Q.; Lin, S.-L.; Warnick, K. F.; Tolley, H. D.; Lee, M. L. J. Chromatogr. A 2003, 985, 455-462.
95. Humble, P. H.; Kelly, R. T.; Woolley, A. T.; Tolley, H. D.; Lee, M. L. Anal. Chem. 2004, 76, 5641-5648.
96. Kelly, R. T.; Woolley, A. T. J. Sep. Sci. 2005, 28, 1985-1993.
97. Myers, P.; Bartle, K. D. J. Chromatogr. A 2004, 1044, 253-258.
98. Kelly, R. T.; Pan, T.; Woolley, A. T. Anal. Chem. 2005, 77, 3536-3541.
99. Monnig, C. A.; Jorgenson, J. W. Anal. Chem. 1991, 63, 802-807.
100. Kelly, R. T.; Woolley, A. T. Anal. Chem. 2003, 75, 1941-1945.

SUMMARY OF INVENTION

An aspect of the invention is a general approach for solvent bonding of polymeric substrates using a phase-changing sacrificial material. Microchannels are imprinted, molded, etched, or otherwise formed in a substrate of a suitable polymer. The microchannels are then filled with a liquid, which forms a sacrificial layer upon solidification. After solvent bonding or sealing a top cover over the filled microchannels, the device is heated above the melting temperature of the sacrificial material to enable its facile removal as a liquid.

In a more particular aspect of the invention, channels in an embossed polymer piece (e.g. poly(methyl methacrylate) (PMMA)) are filled with a heated liquid (e.g., paraffin wax) that cools to form a solid sacrificial material at room temperature. The sacrificial material prevents the bonding solvent (e.g., acetonitrile) and softened polymer from filling the channels. Once the sealing step is complete, the sacrificial material is melted and removed, leaving enclosed microfluidic capillaries.

Exemplary solvent bonded substrates have been made that can withstand internal pressures >2250 psi, much higher than thermally bonded PMMA made by prior-art processes. These solvent bonded substrates have demonstrated functionality as microfluidic systems performing rapid and high-resolution microchip capillary electrophoresis (CE) separations of fluorescently labeled amino acids and peptides. These separations compare favorably with glass microchip CE of peptide mixtures,[26-28] and surpass those previously done on polymer microchips[29-32] in terms of both speed and efficiency. Amino acid and peptide mixtures were separated in <15 s, with >40,000 theoretical plates in a 2.5 cm separation distance. Separations have been performed in electric fields as high as 1500 V/cm, the highest reported to date for polymer microchips. Finally, a single device was used for more than 300 runs over a three-month period without a decrease in separation performance, demonstrating long device lifetimes.

In general, solvent bonding is an appealing alternative to conventional thermal bonding techniques. Also known as solvent welding or solvent cementing, solvent bonding is a simple and economic method used commercially for joining polymeric materials. When a solvent is applied to the plastic, it softens and partially dissolves the substrate surfaces, allowing the polymer chains increased freedom of movement. If two solvent-softened pieces are then brought together under pressure, the material flows, and van der Waals attractive forces occur between the polymer chains in each substrate, which intermingle and diffuse into one another, such that after the solvent evaporates from the joined area, the two pieces remain sealed together.[59] Unlike thermal bonding, solvent welding can be performed at or near room temperature, better preserving channel and surface integrity, while still allowing uniform composition of the device. Also, solvent bonding should allow facile surface modification prior to channel enclosure. Such functionalization may control electroosmotic flow and analyte adsorption, or provide attached chemical or biological groups on microchannel walls. In addition, the ability to construct microchip CE systems from different polymer substrates using simple room temperature bonding should increase the range of devices available for microfluidic experimentation.

Utilizing solvent bonding to prepare microdevices, according to the invention, is a relatively straightforward procedure. Reference is made to FIG. 1, which illustrates an exemplary method of the invention. In this example, an etched silicon template is used to thermally imprint a polymer substrate with the desired channel pattern. Following this step, a thin piece of poly(dimethylsiloxane) (PDMS) with small holes corresponding to the locations of the imprinted channel wells is reversibly sealed as a cover layer to the substrate (FIG. 1a). Next, to protect the channel during solvent bonding, the enclosed capillaries are filled with a sacrificial material (FIG. 1b). In addition to being impervious to the bonding solvent, the sacrificial material must also transition easily from the solid to the liquid state near room temperature, remain smooth upon solidification, and interact minimally with both the substrate and the PDMS. To fill the channels, the sacrificial substance is warmed above its melting point, a small volume of the molten material is applied to the all but one of the PDMS access holes, and vacuum is applied at the unfilled opening, which causes the liquid to fill the entire microchannel network. Once the substrate has cooled and the sacrificial material has solidified, the elastomer is removed carefully (FIG. 1c). A thin layer of solvent is spread across the surface (FIG. 1d), and a non-imprinted polymer top cover with similar dimensions to the imprinted substrate is aligned and affixed with added pressure until a firm bond is established (FIG. 1e). Finally, once bonding is complete, heat or an appropriate solvent is used to remove the sacrificial material (FIG. 1f).

Suitable materials for the substrate include any suitable polymeric plastic, wherein suitable microchannels can be formed and the substrate solvent bonded to the top cover. The top cover is of the same or different materials. Suitable materials include, but are not limited to, PMMA substrates, polycarbonate (PC) and polyethylene terephthalate-glycol (PETg).

While PMMA is a widely used hard polymer material for microfabriation, PC and PETg also possess unique characteristics beneficial for miniaturized devices. For example, PMMA's glass transition temperature (106° C.) is too low to support high temperature cycling for on-chip reactions, such as amplification through PCR, but PC boasts a high glass transition temperature (150° C.) that is well suited for reactions requiring thermal cycling up to ~100° C. Also, compared to PMMA, which is more brittle and easily scratched, PC is a remarkably strong and durable polymer. Unfortunately, despite its high optical clarity, PC tends to degrade with exposure to UV light and has a stronger intrinsic fluorescence background than PMMA or glass.[59] PC is also very hydrophobic: when aqueous solutions are forced into channels in this plastic, the surface is not wetted uniformly.[61] In Table 3 is summarized the properties of certain polymers.

Like PC, polyethylene terephthalate (PET) is a durable polymer, with better impact resistance than PMMA. PET is the most common of the thermoplastic polymers and has excellent optical transparency. Unlike PC, PET is laser machinable and can be imprinted at moderate temperatures. However, this lower glass transition temperature makes PET unsuitable for continued use at or over 65-70° C. Like PC, PET is UV sensitive and also exhibits brittleness and premature aging, though incorporating glycol modifiers into the plastic (PETg) helps reduce these effects.[62] Table 3 compares the advantages and disadvantages of PMMA, PC, and PETg.

TABLE 3

Characteristics of different polymers.

| | PMMA | PC | PETg |
|---|---|---|---|
| Advantages | Least hydrophobic<br>Least UV sensitive<br>Good optical properties<br>Laser machinable | Strong and durable<br>High glass transition temperature (150° C.)<br>Good optical clarity | Good optical properties<br>Better impact resistance than PMMA<br>Laser machinable |

TABLE 3-continued

Characteristics of different polymers.

| | PMMA | PC | PETg |
|---|---|---|---|
| Disadvantages | More brittle and easily scratched than PC<br>Moderate glass transition temperature (106° C.) | Strong intrinsic fluorescent background<br>Not laser machinable<br>Hydrophobicity<br>UV sensitive | Low glass transition temperature (80° C.)<br>Brittleness and premature aging<br>UV sensitive |

Table 4 summarizes the different solvent bonding variables and what materials were studied for each. Materials for polymer substrates and top covers, for sacrificial materials and for solvents that were proven successful under particular conditions are indicated by a ☺. The other substances for sacrificial material and solvents may also prove suitable under different conditions, or in different combinations of substances for the sacrificial material and solvent. It should be noted that the necessary properties for the polymeric material of the substrate, polymeric material of the top cover, the properties of the sacrificial material, and the properties of the solvent are necessarily intertwined, and the properties of the combination as a whole have to examined. A successful combination of any of the materials below, or any other suitable material is contemplated by the invention.

TABLE 4

Solvent bonding needs and options.

| | Requirements | Studied |
|---|---|---|
| Polymer Substrate | Easily imprinted with Si template<br>Inexpensive<br>Seals to elastomer<br>Doesn't interfere with chemical analysis | PMMA☺<br>PC☺<br>PETg☺ |
| Sacrificial Material | Transitions from solid to liquid near room temperature<br>Doesn't interact with polymer/elastomer<br>Appropriate viscosity<br>Forms smooth, even channels<br>Solubility different from substrate | Paraffin wax☺<br>PEG 3350<br>PEG 1450<br>PEG 400<br>Eicosane<br>Lauric acid<br>Solid vegetable oil<br>Soy wax<br>Crème ™ wax ☺ |
| Solvent | Dissolves substrate but not sacrificial material<br>Appropriate rate for dissolving substrate | Acetonitrile☺<br>Acetone☺<br>Ethylene glycol<br>Dichloromethane<br>Phenyl acetate☺<br>10% NaOH solution<br>Dimethyl sulfoxide (DMSO) |

Another aspect of the invention is a method for interfacing ionically conductive membranes with microfluidic systems using phase-changing sacrificial materials. This aspect is a modification of the basic method above for solvent bonding of polymer microdevice substrates,[98] where imprinted microchannels in poly(methyl methacrylate) (PMMA) are filled with a phase-changing sacrificial material (PCSM), after which solvent is applied to the surface. A cover plate or top cover is placed in contact with the patterned substrate to allow a robust seal to form, and then the PCSM, which prevents solvent from filling the microchannels during bonding, is melted and removed. More generally, PCSM placeholders could be applied in other microfluidics applications, such as integrating membranes with microchannels.

In this aspect of the invention is a method for in situ polymerization of membranes interfaced with microfluidic networks, based on the PCSM approach developed for making solvent-bonded microchips.[98] The procedure involves placing a prepolymer solution over PCSM-filled microchannels, polymerization and then sacrificial material removal.

Microchip EFGF (μ-EFGF) devices having semi-permeable membranes have been fabricated using this approach, and the smaller dimensions of these μ-EFGF systems relative to other changing CSA-based EFGF platforms resulted in decreased laminar flow dispersion and narrower analyte bands. Protein preconcentration microdevices based on semi-permeable membranes have also been designed, where imprinted channels in PMMA are interfaced with a semi-permeable membrane using a PCSM in a manner similar to that for μ-EFGF systems. Importantly, greater than 10,000-fold protein sample enrichment has been achieved in these membrane-integrated PMMA microchips.

The microchip EFGF devices according to the invention have offered improved protein focusing performance compared with capillary-based systems. In addition, these EFGF microchips can separate peptide samples with resolution similar to what is obtained in capillary electrophoresis microdevices, and the micro-EFGF systems enrich analytes by a factor of >150. Finally, hydrogel-integrated microfluidic devices have been fabricated that can concentrate protein samples over 10,000-fold. Interfacing microchannels with ion-permeable membranes has great potential to enhance microchip analysis of biomolecules.

(C) The same PMMA/PDMS assembly as (A), but 80 min later when excess sacrificial material had dissolved in the PDMS, leaving well-defined channels.
(D) A completed microchip made from the PMMA substrate in (A,C) after solvent bonding and sacrificial material removal.

Figure 5:
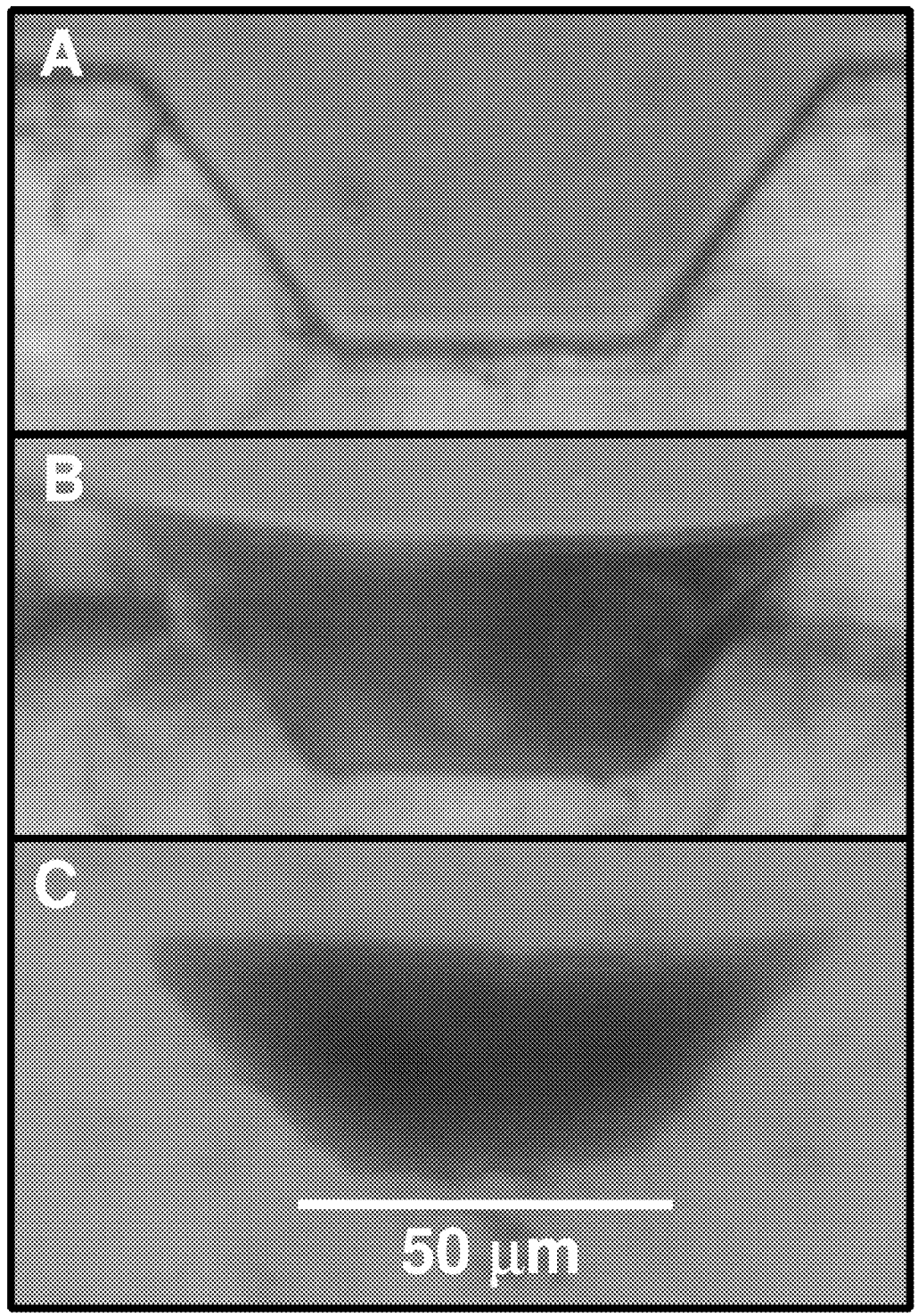

FIG. 5 shows channel cross-sectional photomicrographs at various fabrication stages.
(A) Imprinted channel.
(B) Imprinted channel filled with wax and having the PDMS removed. (A-B) were obtained by scoring and then fracturing the substrates, which led to some roughness in the surrounding bulk PMMA.
(C) Bonded device after wax removal; the slightly roughened appearance around the channel perimeter was the result of using a diamond-tipped circular saw to obtain the cross-section. The scale bar in (C) applies to all images.

Figure 6:
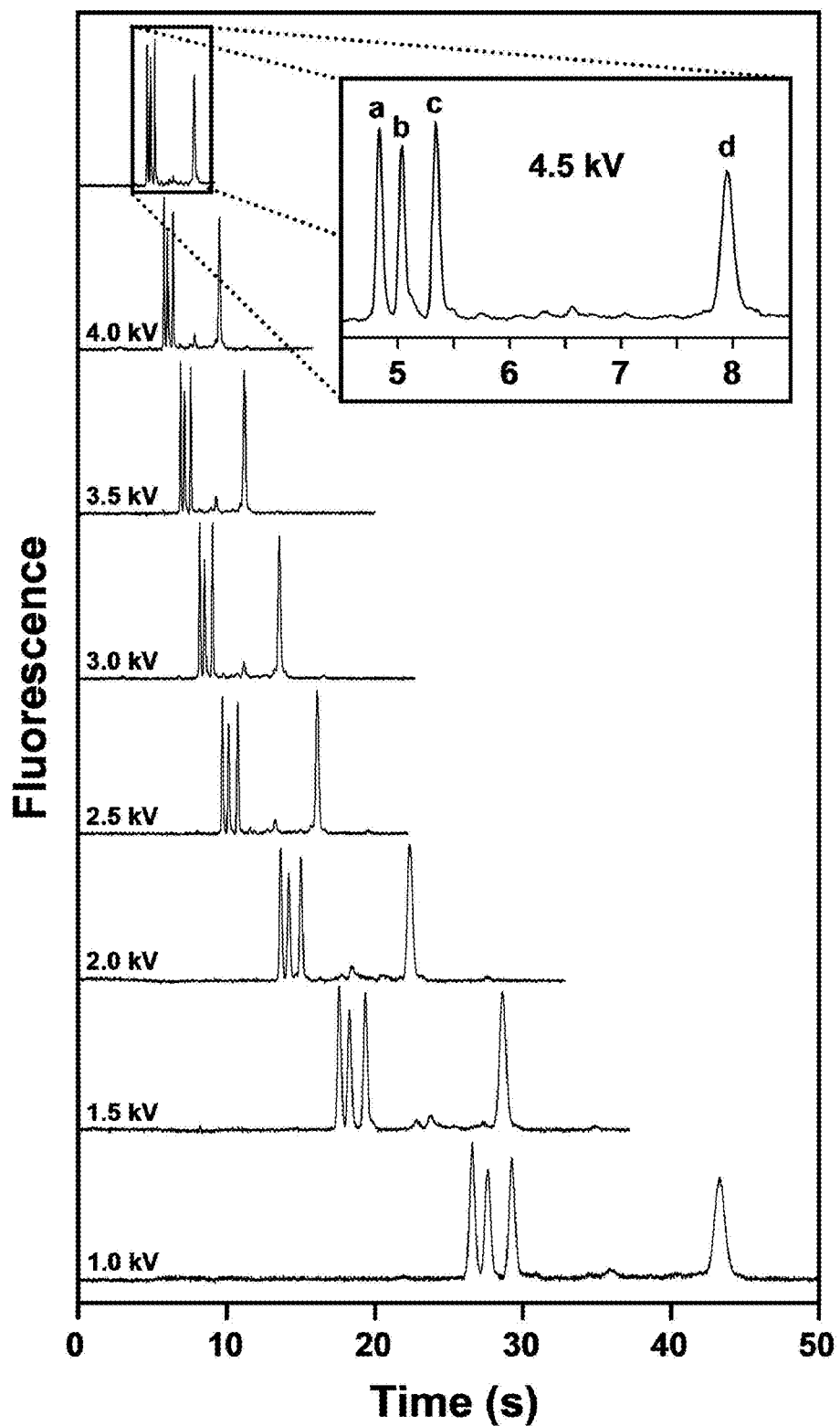

FIG. 6 is a graph that shows electropherograms of a mixture of FITC-amino acids at different separation voltages (shown on the figure). The injection voltages from bottom to top were: +300 V, +450 V, +600 V, +750 V, +900 V, +1050 V, +1150 V, and +1250 V. Amino acid concentrations were 75 nM, and the run buffer was 10 mM carbonate, pH 9.2, with 0.5% (w/v) HPC. Peaks are: (a) Gly, (b) Asn, (c) Phe, and (d) Arg.

Figure 7:
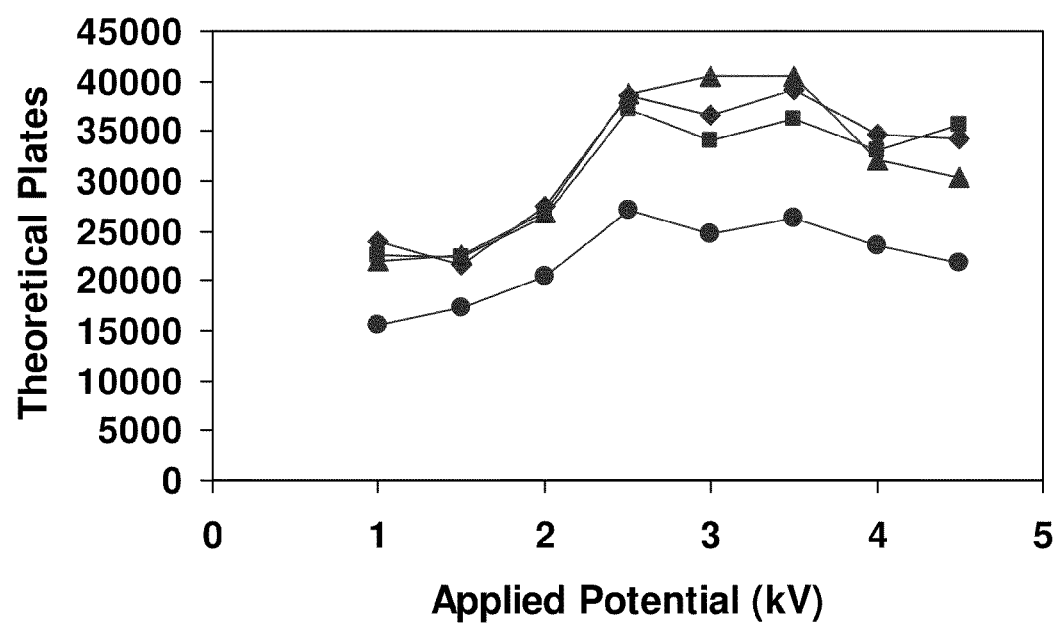

FIG. 7 is a graph showing theoretical plates vs. applied voltage for the amino acid separations shown in FIG. 6. Legend: Gly (♦), Asn (■), Phe (▲), Arg (●).

Figure 8:
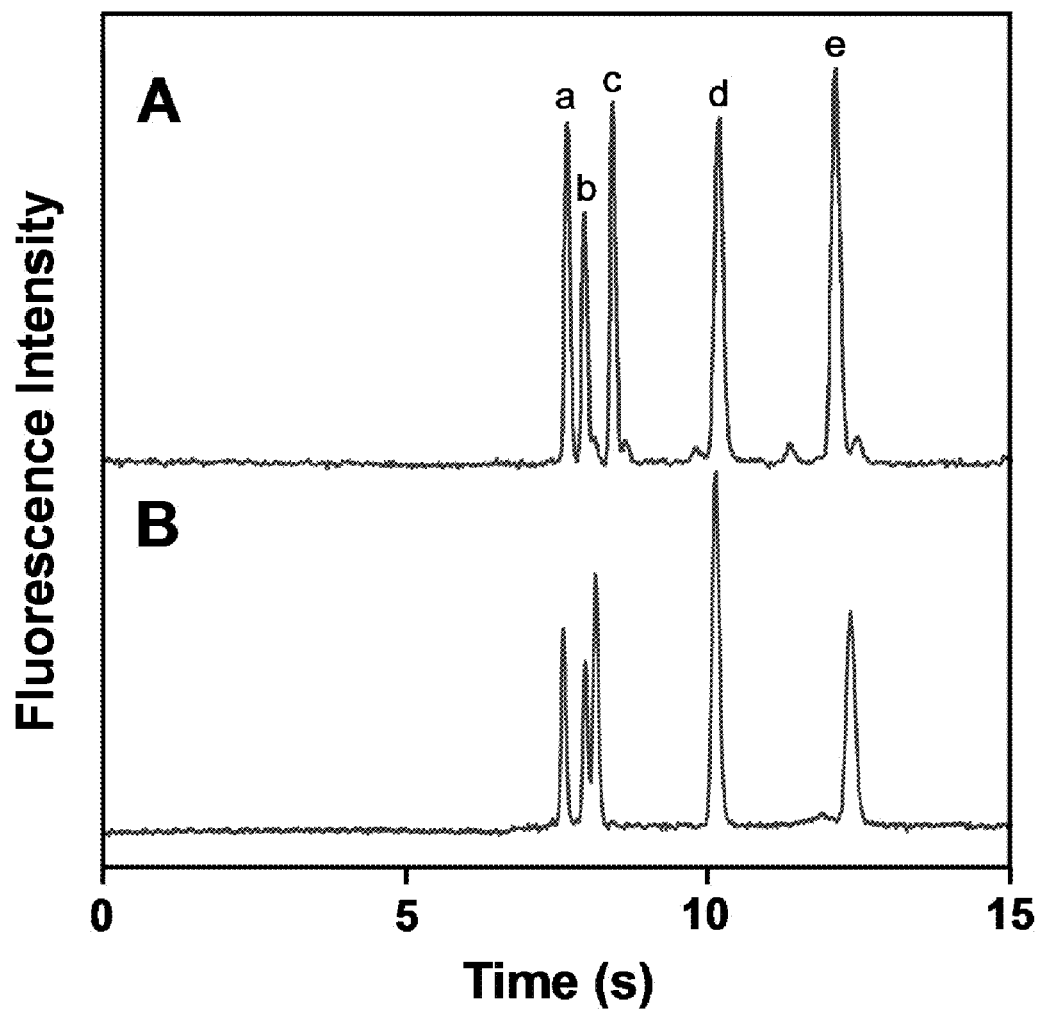

FIG. 8 is a graph showing separation of FITC-labeled amino acids in 10 mM carbonate buffer, pH 9.2 with (A) and without (B) 0.5% (w/v) HPC in the run buffer. Peaks are: (a) Gly, (b) Asn, (c) Phe, (d) FITC, and (e) Arg. The injection voltage was +800 V, and the separation voltage was +3.0 kV.

Figure 9:
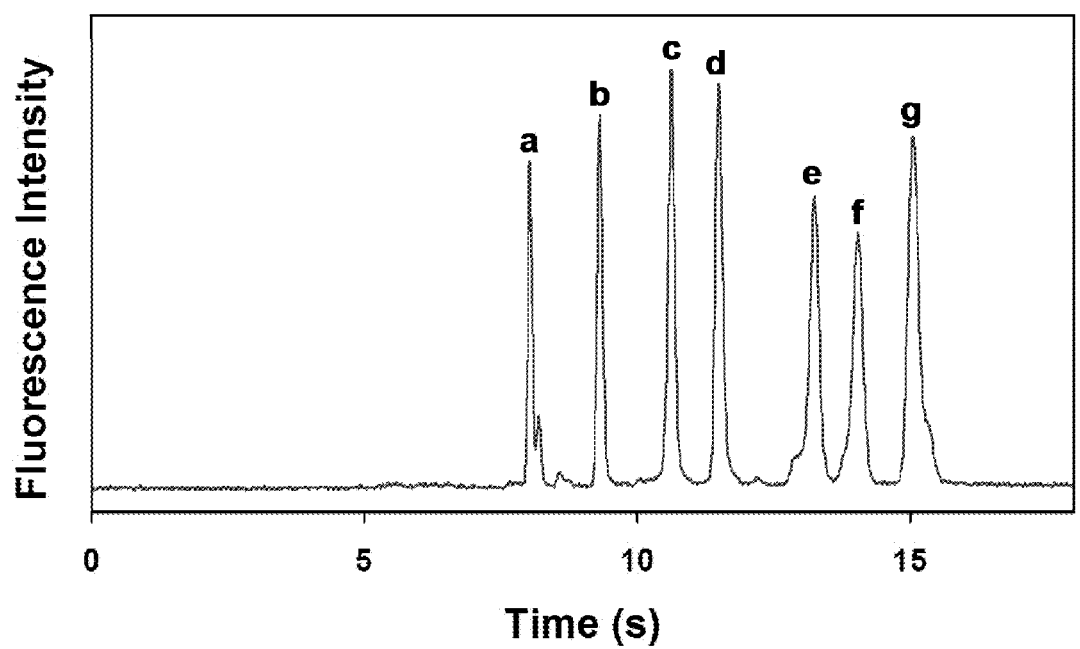

FIG. 9 is a graph showing separation of FITC-labeled peptides. Peaks are: (a) FLEEI; (b) FA; (c) FGGF; (d) Leu enkephalin; (e) angiotensin II, fragment 3-8; (f) angiotensin II; and (g) GGYR. The buffer composition and voltages were the same as in FIG. 8A, and the concentration of all peptides was 110 nM.

Figure 10:
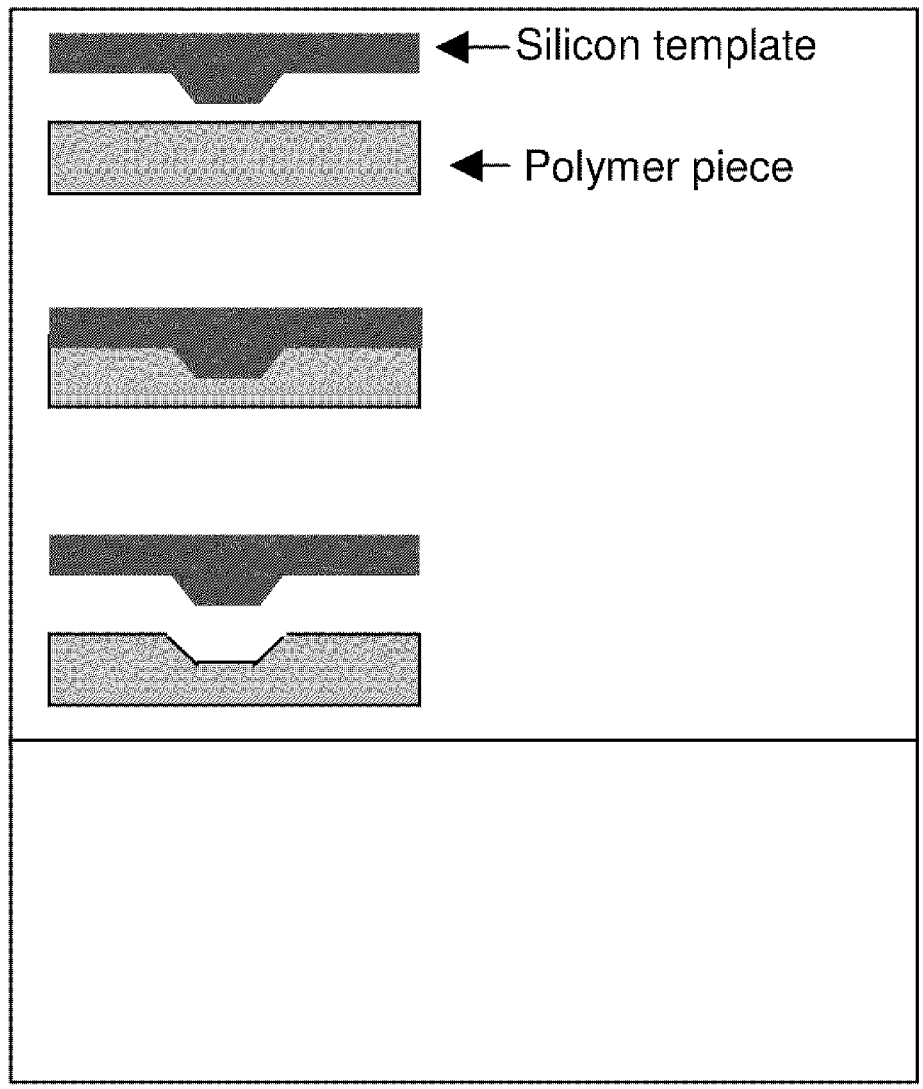

FIG. 10 is a schematic showing channel imprinting in polymeric substrates. A polymer piece and a silicon template featuring a raised channel design on the surface are combined using pressure and either heat or solvent to transfer the channel pattern into the plastic.

Figure 11:
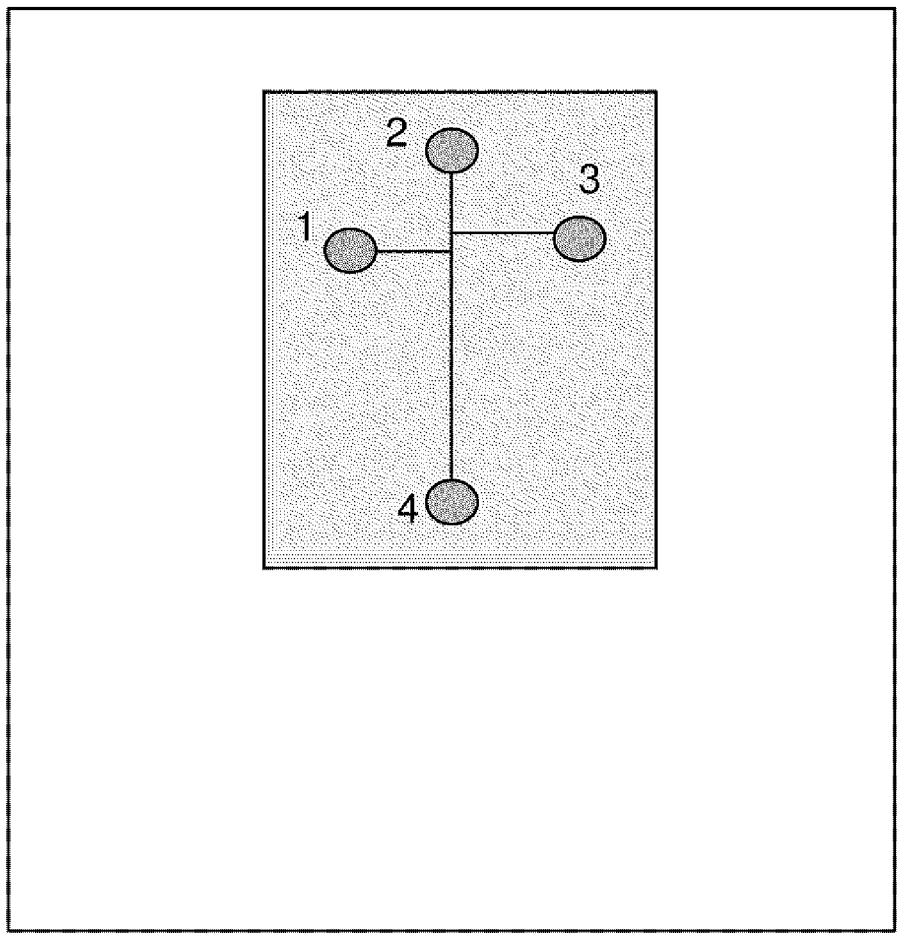

FIG. 11 is schematic showing a microchip CE device layout.

Figure 12:
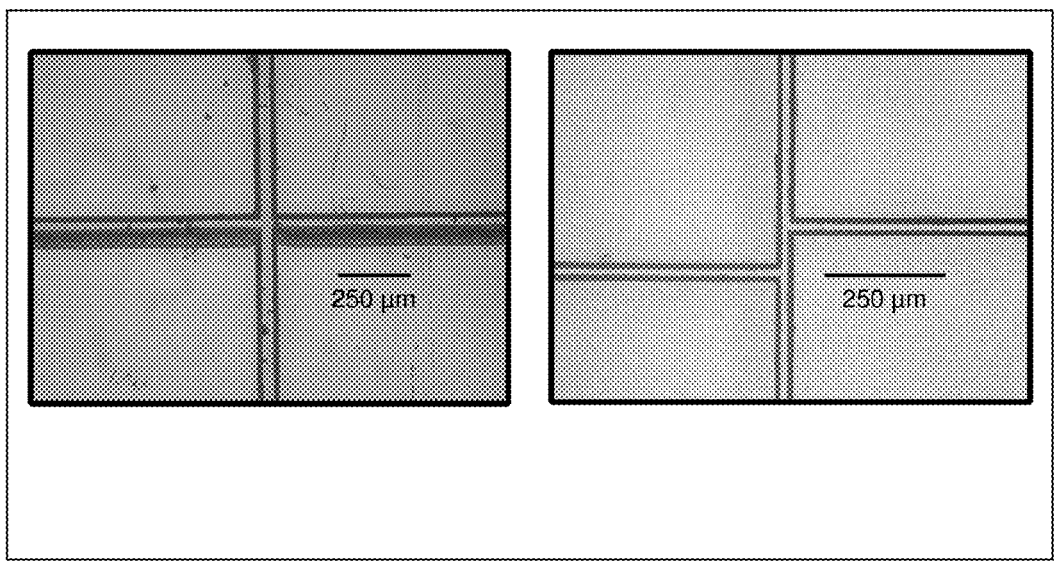

FIG. 12 shows photographs of thermally imprinted PC channels. The shifting was minimized in the image on the right by removing the substrate from the template just after the polymer was cooled below the glass transition temperature.

Figure 13:
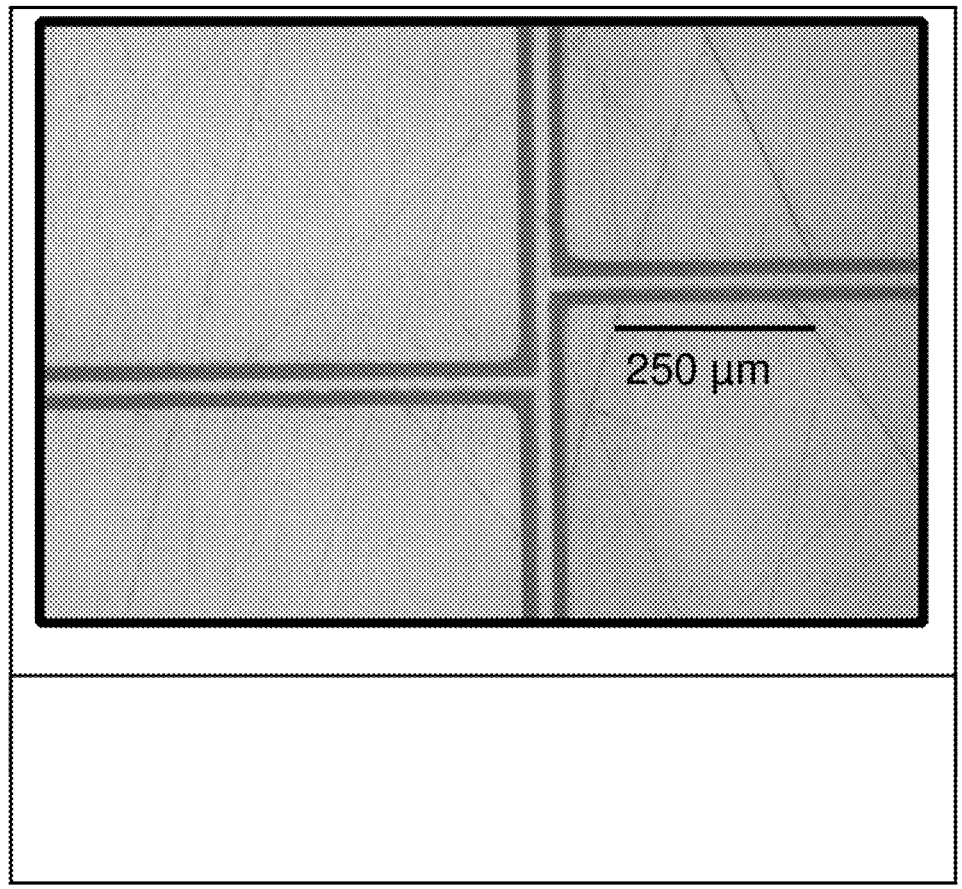

FIG. 13 shows a photograph of a thermally imprinted PETg channel.

Figure 14:
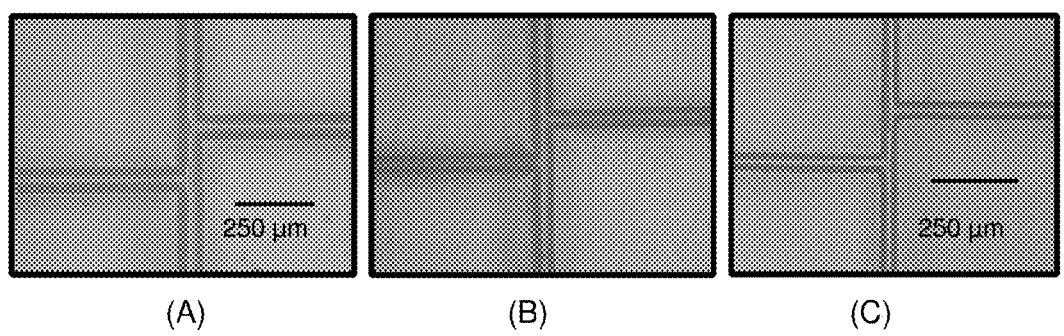

FIG. 14 shows photographs of solvent-imprinted channels in (A) PMMA, (B) PC, and (C) PETg.

Figure 15:
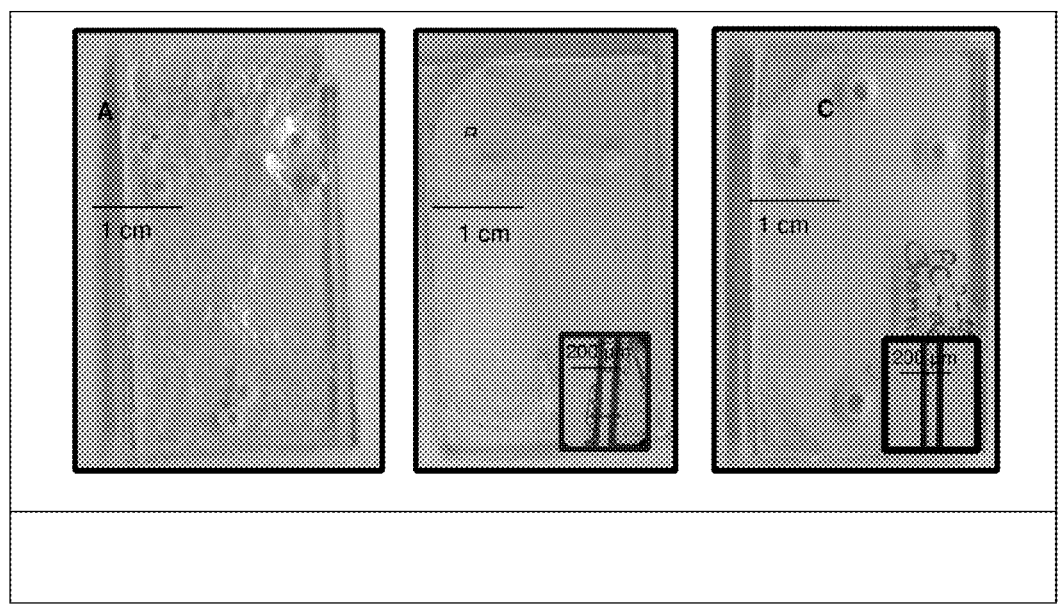

FIG. 15 shows photomicrographs illustrating surface damage in solvent-imprinted, solvent-bonded PC devices. (A) Extreme damage, (B) microscopic damage, (C) no damage.

Figure 16:
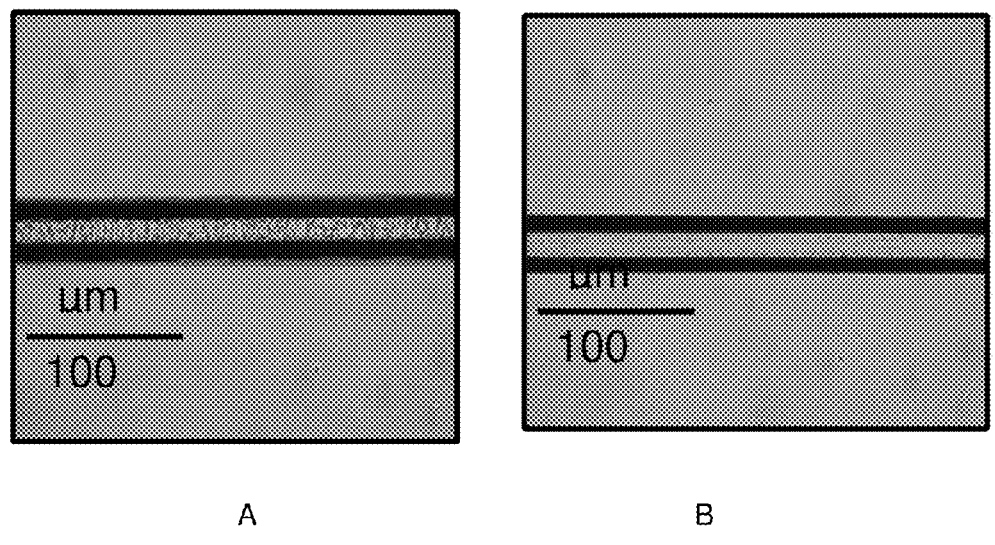

FIG. 16 shows photographs of solvent-bonded microchannels made with (A) paraffin wax and (B) Crème wax as the sacrificial material.

Figure 17:
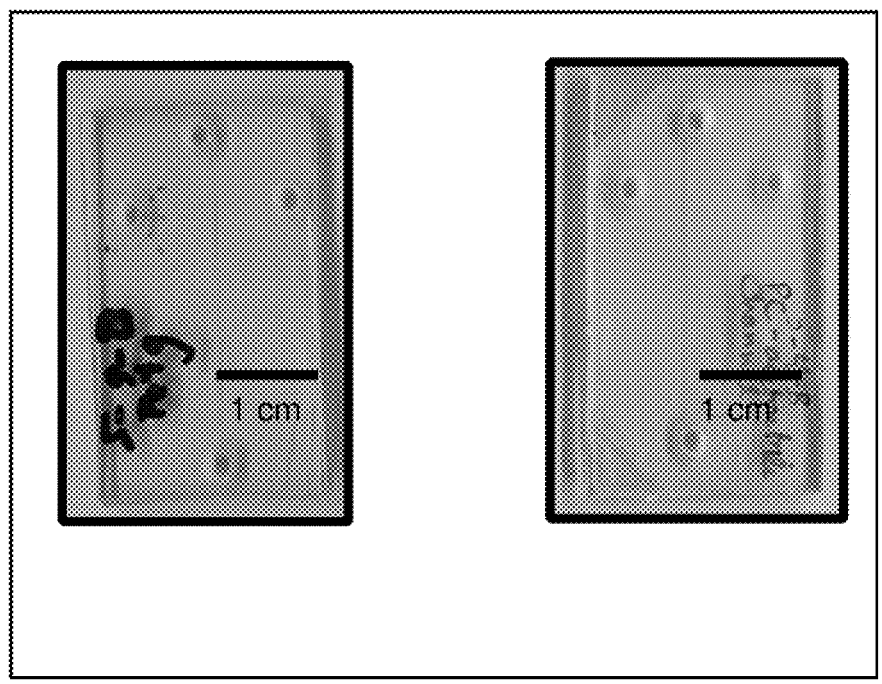

FIG. 17 shows photographs of solvent-bonded PETg (left) and PC (right) devices.

Figure 18:
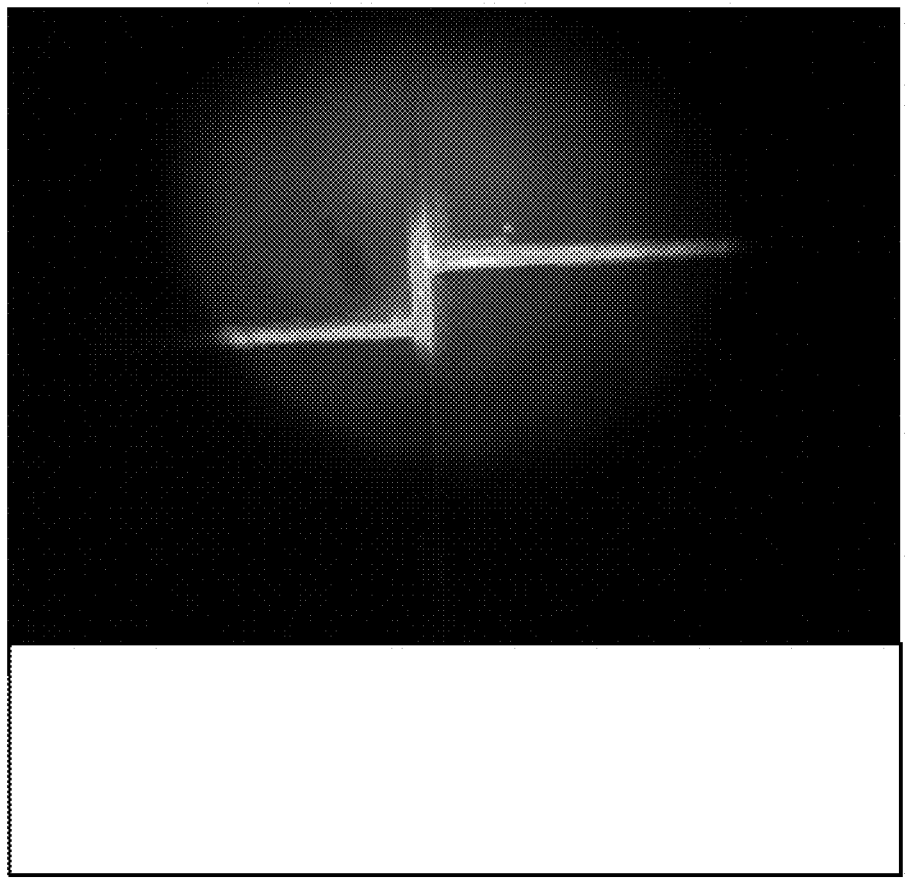

FIG. 18 is a photograph showing fluorescein in the injection region in a solvent-bonded PETg device.

Figure 19:
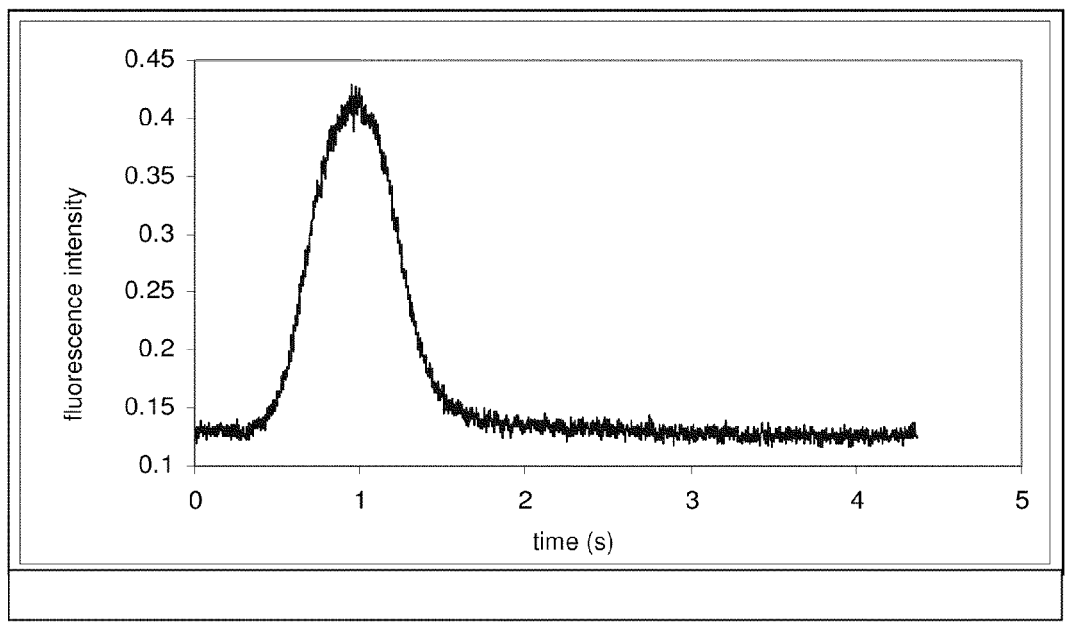

FIG. 19 is a graph showing an injected fluorescein peak observed in a solvent-bonded PC device.

Figure 20:
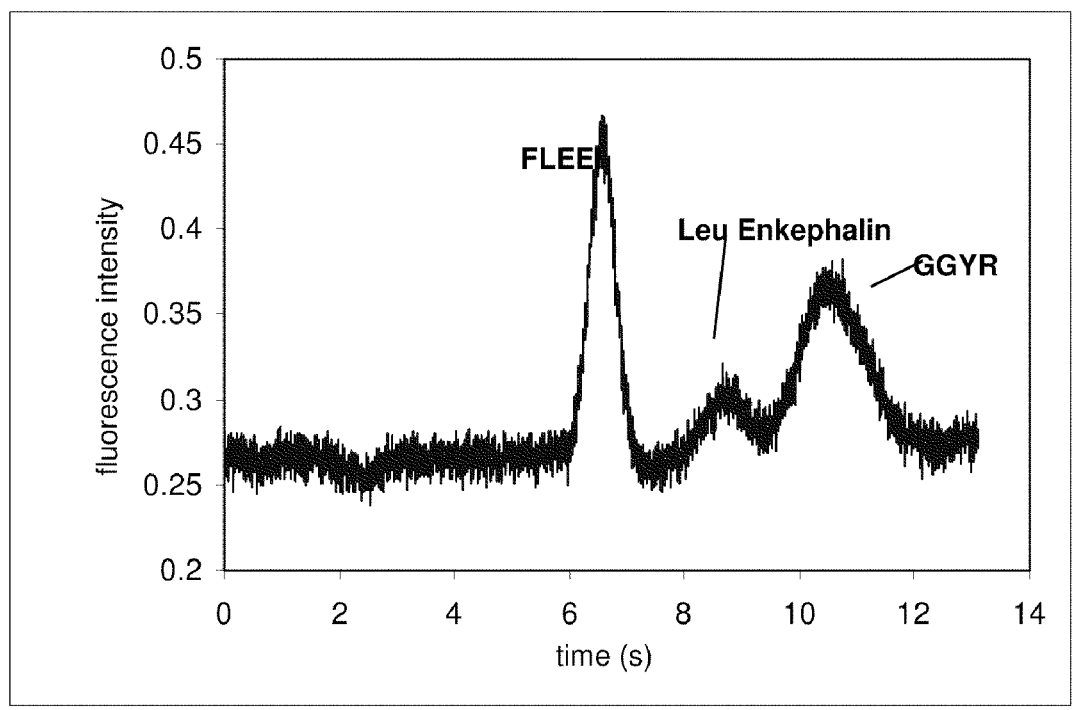

FIG. 20 is a graph showing CE separation of three peptides on a solvent-bonded PC device.

Figure 21:
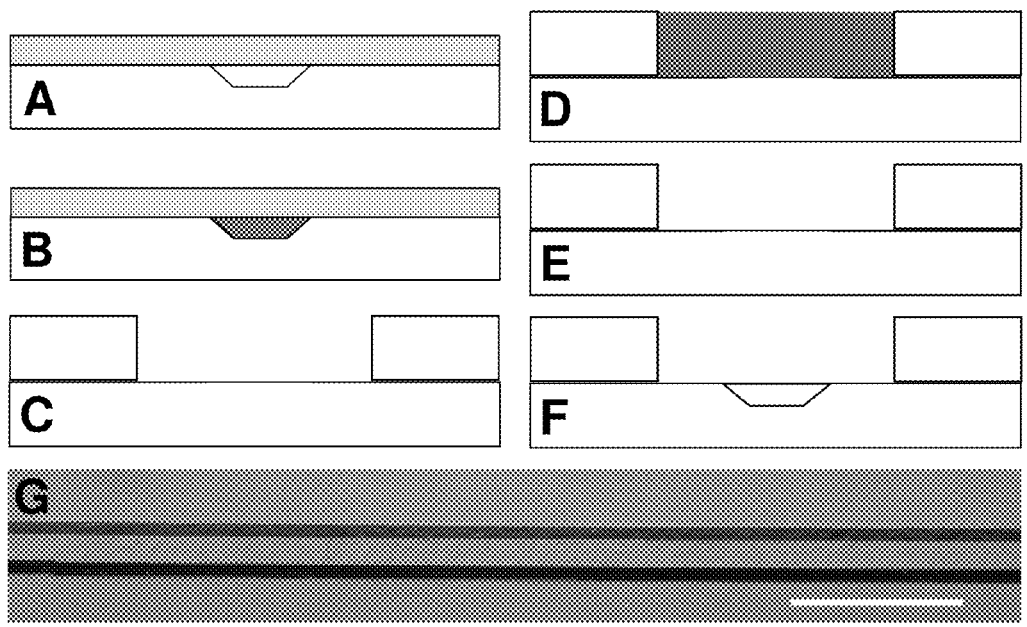

FIG. 21 is a schematic flow sheet showing PCSM fabrication procedure for in situ polymerization of an semipermiable membrane interfaced with a microfluidic system.
(A) PDMS (gray) is placed on an imprinted PMMA substrate (white), forming enclosed microchannels.
(B) The assembly is heated, and liquid PCSM (white with gray stripes) fills the microchannels.
(C) The device is cooled to solidify the PCSM (gray with white stripes), the PDMS is removed, and a PMMA substrate with an opening is placed on top.
(D) Prepolymer solution (dark gray) is loaded into the well.
(E) The ion-permeable hydrogel (dark gray with white cross-hatching) is photopolymerized.
(F) The PCSM is melted and removed.
(G) Photomicrograph of a microchannel interfaced with an semipermiable membrane following the above procedure. The scale bar is 250 μm.

Figure 22:
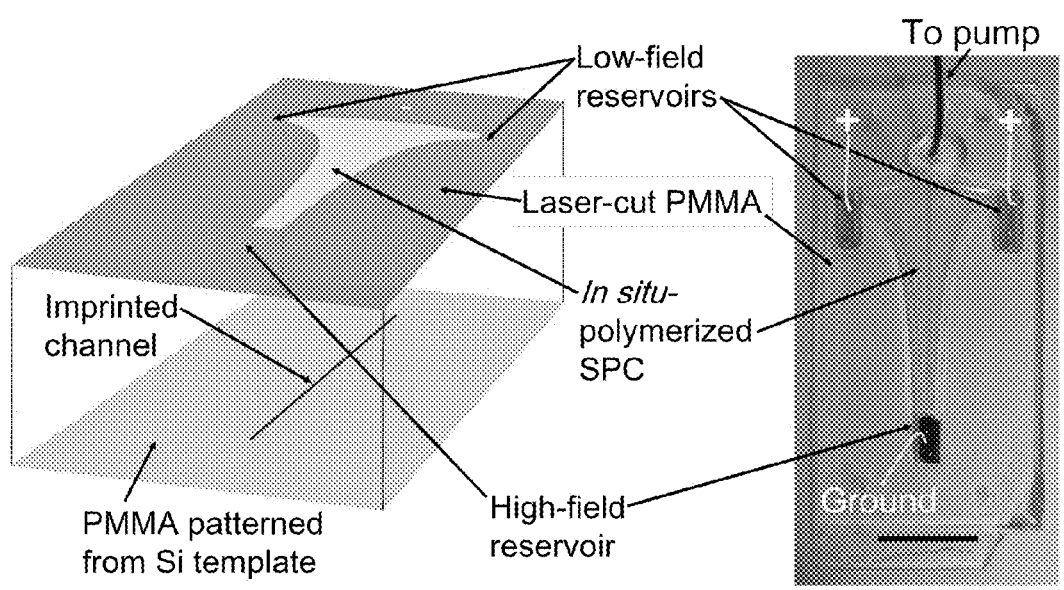

FIG. 22 is a schematic depiction (left, exploded view) and photograph (right) of an EFGF microchip. In the photograph buffer reservoirs and the microchannel were filled with colored solution for enhanced visualization. The scale bar on the photograph is 1 cm.

Figure 23:
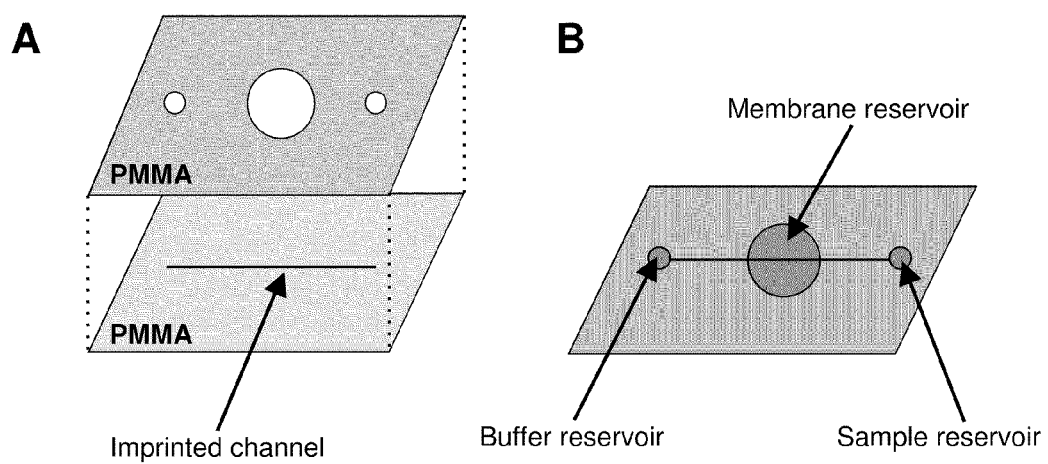

FIG. 23 is a schematic depiction of a membrane-based preconcentration microdevice. (A) Exploded view. (B) Assembled device view. Additional description is in the text.

Figure 24:
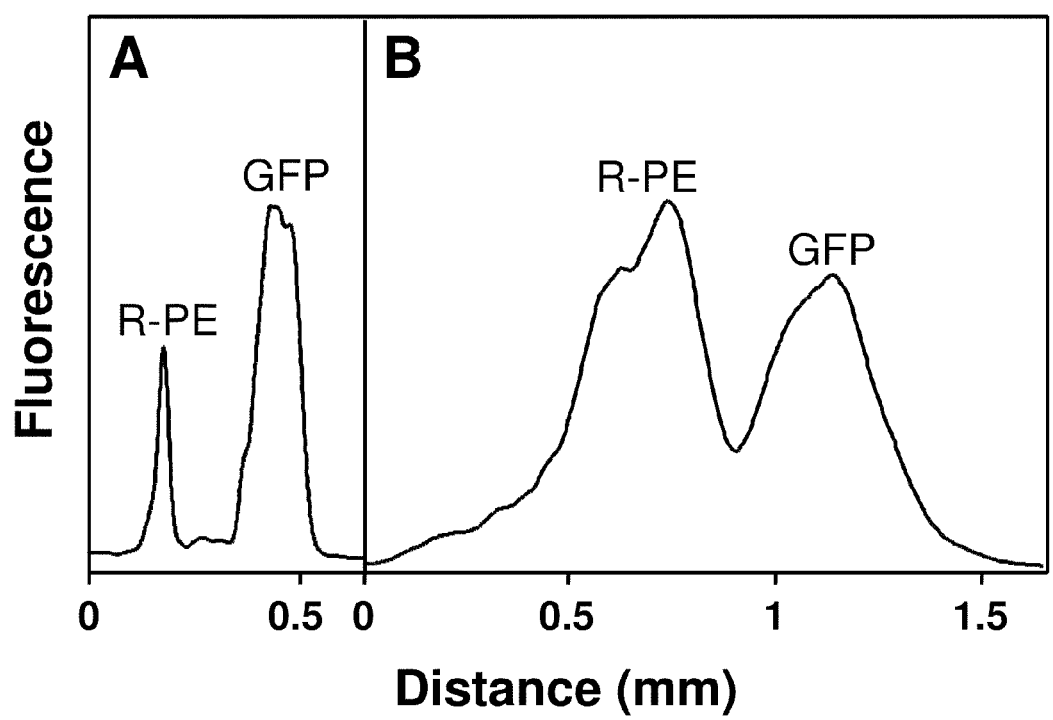

FIG. 24 is a graph showing separation of R-PE and GFP in (A) a μ-EFGF device and (B) a capillary-based EFGF system. In (A) 20 mM Tris, pH 8.7 was used, and the counterflow rate and applied potential were 20 nL/min and +1,000 V, respectively. For (B) the run buffer was 5 mM Tris, pH 8.7, the counterflow rate was 30 nL/min, and the applied potential was +2,000 V. Maximum fluorescence intensities were normalized to be the same in (A-B).

Figure 25:
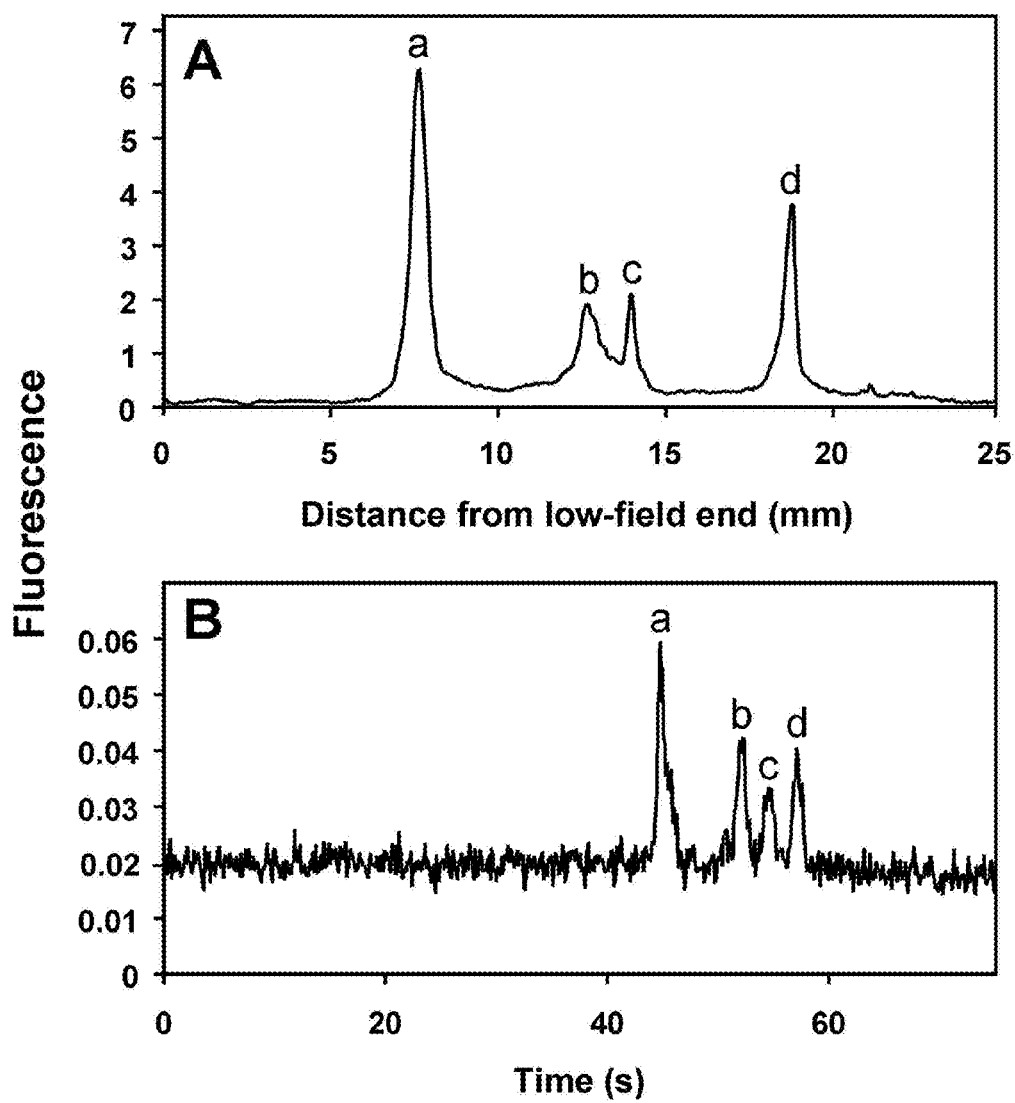

FIG. 25 is a graph showing separation of fluorescently labeled peptides by
(A) μ-EFGF and (B) μ-CE. Peaks are (a) FLEEI, (b) FGGF, (c) angiotensin II, fragment 3-8, and (d) GGYR. Initial peptide concentrations were 50 nM, and the run buffer was 100 mM Tris (pH 8.1) with 0.5% HPC. The separation potential was 200 V in (A) and 1,000 V in (B). The counterflow rate in (A) was 5 nL/min.

Figure 26:
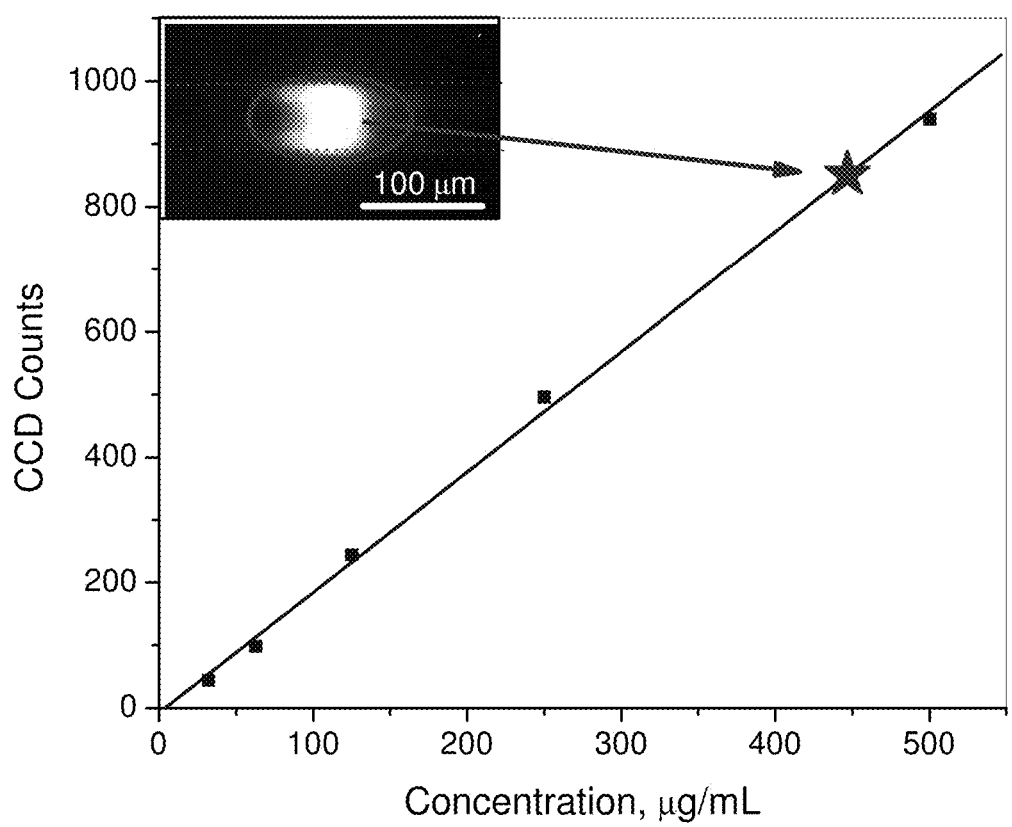

FIG. 26 is a graph showing a calibration curve for CCD signal as a function of R-PE concentration in standard solutions. (Inset) CCD image of 40 ng/mL R-PE concentrated at the membrane reservoir for 40 min; the signal from this image corresponds to the star on the calibration curve.

DETAILED DESCRIPTION

Example 1

Micro Fabrication

Figure 1:
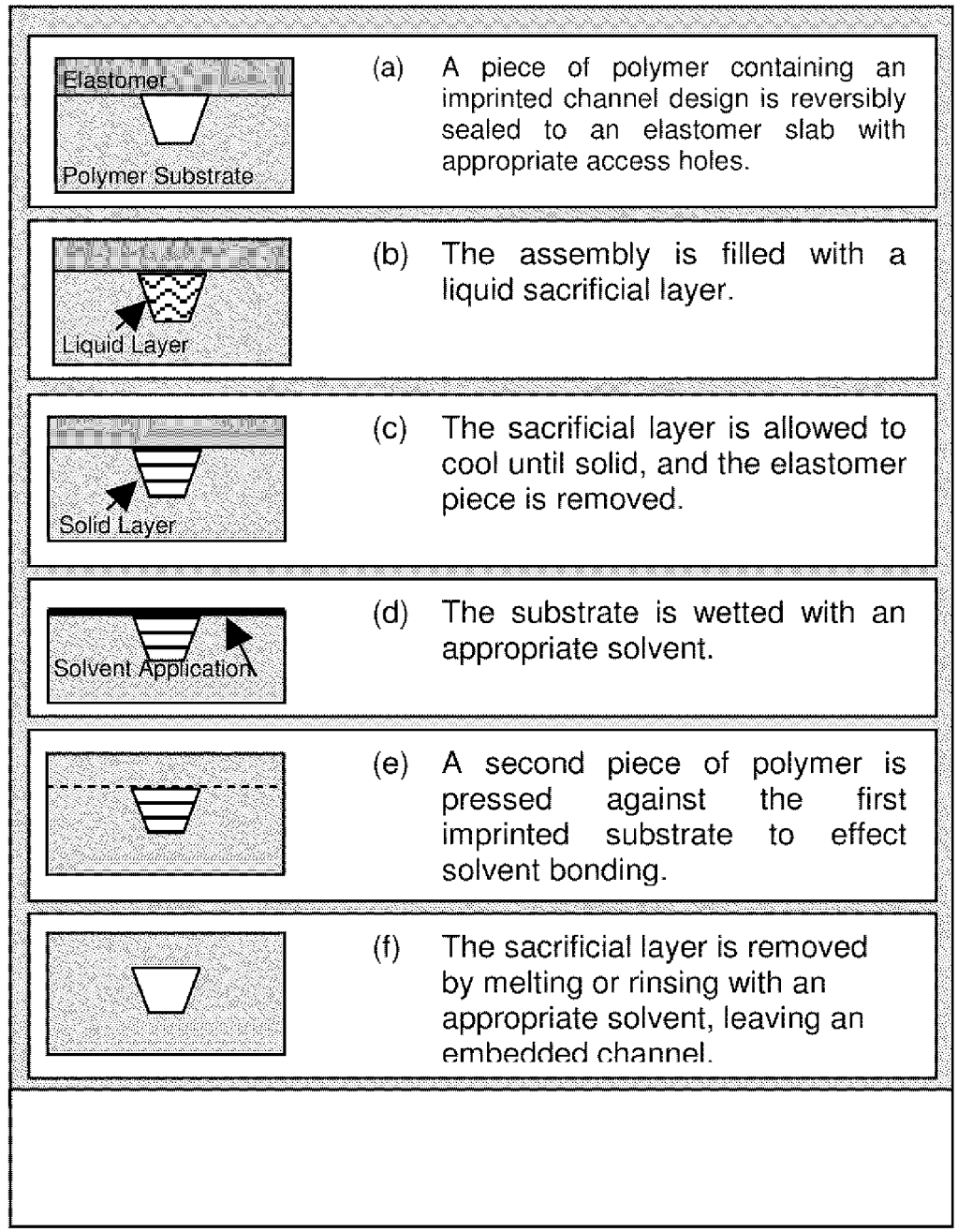
FIG. 1 is a schematic diagram illustrating a method of the invention where solvent bonding is applied to enclose capillaries in microdevices.
Figure 2:
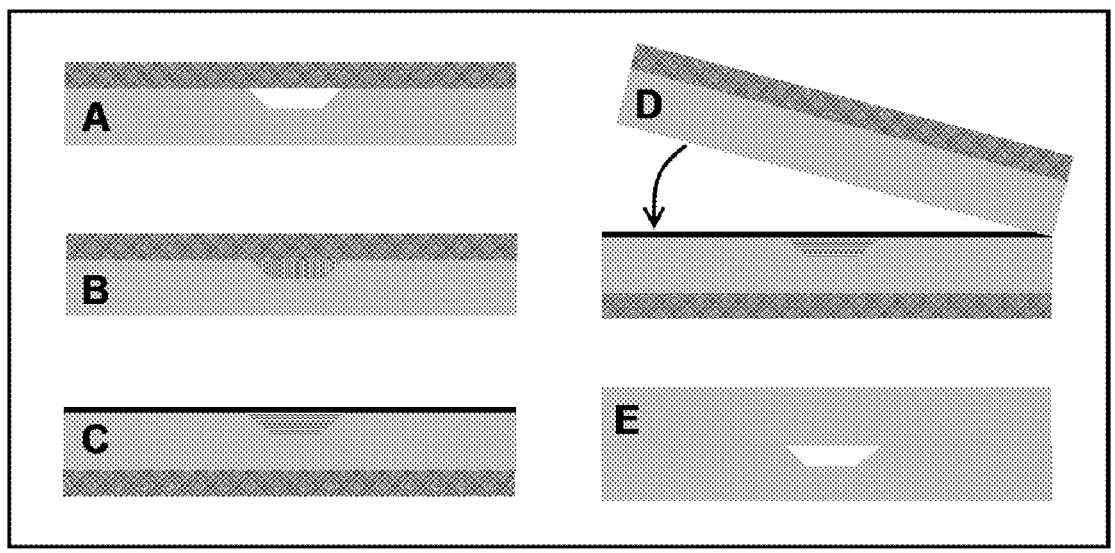
FIG. 2 is a schematic illustrating a method of the invention, where solvent bonding is used to create microfluidic systems in polymers, where;
(A) A PDMS slab (dark gray with white crosshatching) is sealed to an imprinted PMMA substrate (gray), temporarily forming enclosed microchannels.
(B) The assembly is heated, and liquid paraffin wax (gray with vertical lines) fills the microchannels.
(C) The device is cooled to solidify the wax (gray with horizontal lines), and the PDMS slab is removed and placed on the opposite side of the PMMA to protect the device exterior. The patterned side of the PMMA is then coated with acetonitrile (black).
(D) A second, blank PMMA piece, which also has PDMS protecting its exterior, is pressed against the acetonitrile-coated PMMA for 2 min to effect bonding.
(E) The device is heated to melt the sacrificial material, which is removed by a combination of applied vacuum and dissolution in cyclohexane.
Figure 3:
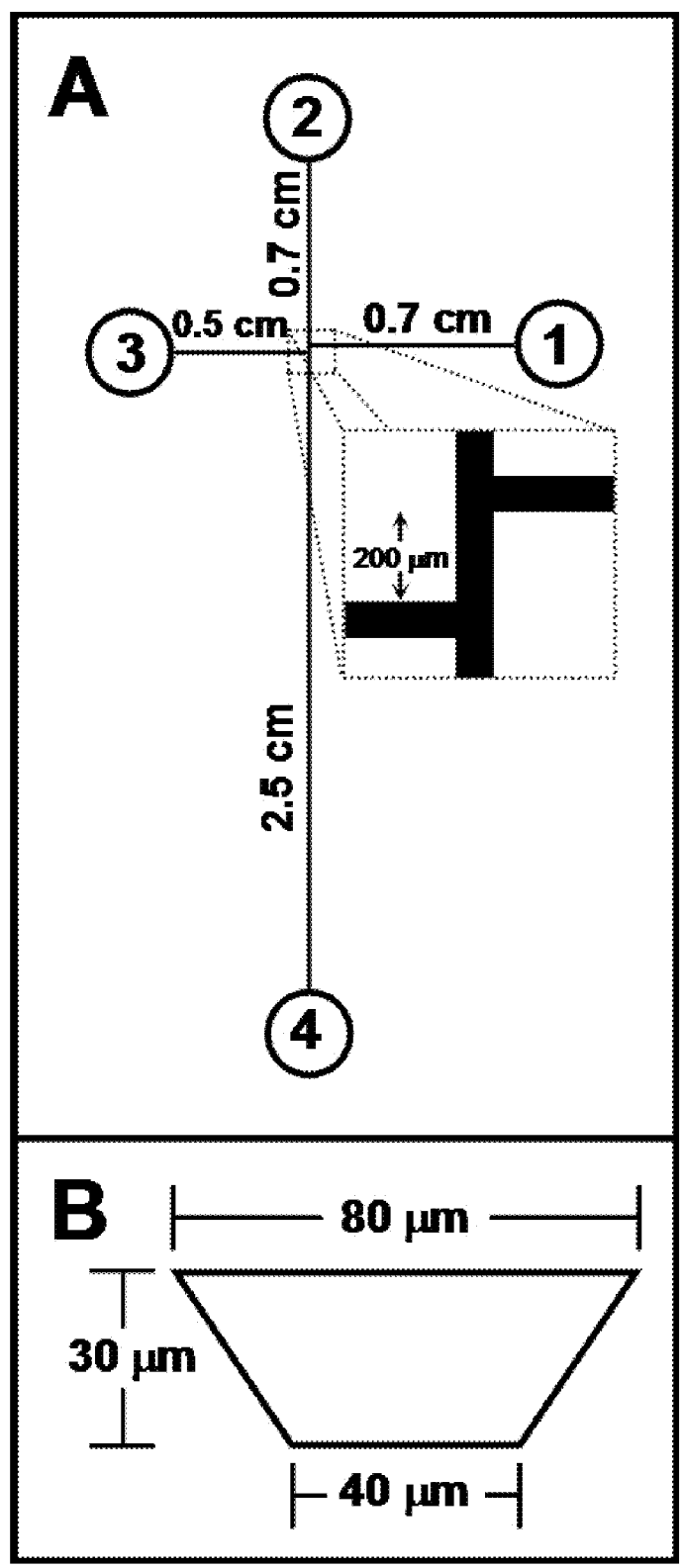
FIG. 3 is a schematic of a microchip layout, showing (A) channel lengths and reservoir numbers, and (B) approximate cross-sectional dimensions.

Reference is now made to FIG. 2. Microchips were made by imprinting raised features from photolithographically patterned and anisotropically etched silicon templates into PMMA substrates using previously described methods.[33] Imprinted PMMA substrates (Acrylite OP-3, Cyro, Rockaway, N.J.) were 1.75"×1"×⅛" and had 3-mm-diameter reservoir holes aligned with the channel ends. A CO$_2$ laser cutter (C-200, Universal Laser Systems, Scottsdale, Ariz.) was used to excise the PMMA substrates from larger sheets and create the reservoir holes. A clean, flat, 1/16"-thick piece of PDMS (Sylgard 184, Dow Corning, Midland, Mich.), which had been cured according to the manufacturer's specifications, was sealed to the patterned side of a PMMA substrate (FIG. 2A), temporarily forming enclosed channels. The PMMA/PDMS assembly was mounted on a glass microscope slide and placed on a heating block at 85° C. (above the melting temperature of the paraffin wax) for 30 s. A pipet was used to quickly transfer melted paraffin wax (melting point: 65° C.; Service Assets, Newport Beach, Calif.) from a heated vial to three of the reservoirs before the melted wax could cool and solidify. After filling three reservoirs with melted wax, vacuum was applied for 1-2 s at the fourth reservoir to ensure that all channels were filled (FIG. 2B) and no air pockets were present, after which the PMMA/PDMS assembly was removed from the hot plate and cooled to room temperature. Next, the channels were inspected under a microscope. If a small amount of paraffin wax had solidified beyond the channels, the imprinted PMMA substrate was left in contact with the PDMS until the paraffin wax outside the channels had dissolved in the PDMS, which was then removed. PDMS was sealed to the non-imprinted side of the PMMA and to a blank piece of $\frac{1}{16}$"-thick PMMA to prevent the solvent from contacting the device exterior. 200-400 µL of acetonitrile were pipetted directly onto the channel-containing substrate (FIG. 2C) to cover the entire surface, and the unpatterned PMMA was placed in contact with the solvent-coated substrate and held together with an applied pressure of 2 psi for 2 min to effect bonding (FIG. 2D). Effective bonding was feasible with as little as 3 µL of acetonitrile per cm$^2$ (~35 µL/device); with volumes over 400 µL/device, excess solvent sometimes flowed from the bonding interface and impaired the optical clarity of the surface. The PMMA pieces were brought together at an angle as shown in FIG. 2D to allow any air bubbles to escape out the side. After the designated time, the applied pressure was released, and the pieces of PDMS were peeled from the device. To remove the sacrificial material from the microchannels (FIG. 2E), 10 µL of cyclohexane were pipetted into each of the reservoirs, and the device was placed on the heating block until the paraffin wax melted. Vacuum was applied at one of the reservoirs to begin removing paraffin wax from the channels, after which that reservoir was refilled with cyclohexane. The same procedure was repeated at each of the reservoirs, and the device was cooled to room temperature. To ensure that all residual sacrificial material was removed, the channels were soaked in cyclohexane for >5 min before vacuuming all liquid from the device. Complete removal of the paraffin wax was verified by the absence of air bubbles upon filling the channels with water, as air bubbles typically became trapped at any points in the channel where the hydrophobic wax was still present. A schematic of the microchip layout and channel dimensions is shown in FIG. 3.

Bond Strength Determination

To measure the internal pressure that could be applied to solvent-bonded substrates, a hole was threaded to accept a $\frac{5}{16}$"×-24 brass fitting in a 1"×1"×$\frac{1}{2}$" piece of PMMA. The threaded piece was solvent bonded to a 1"×1"×$\frac{1}{4}$" PMMA substrate using the same solvent, applied pressure and time as for microchips. For comparison, substrates of the same dimensions were thermally bonded by clamping the pieces together and placing them in an oven at 107° C. After ½ h the thermally bonded PMMA was cooled and evaluated to ensure bonding completeness. If voids were found, the substrates were reclamped, and the bonding procedure was repeated. The brass fitting, which connected the PMMA to a N$_2$ gas cylinder via $\frac{1}{16}$" copper tubing, was threaded into the bonded assemblies. The copper tubing was branched to allow a pressure transducer (MSP-300, Measurement Specialties, Fairfield, N.J.) with a linear response between 0 and 2500 psi to be connected. The regulator on the gas cylinder was opened gradually, increasing the internal pressure in the bonded substrate until either the pieces separated or the maximum pressure of 2250 psi was reached.

Separation and Detection of Amino Acids and Peptides

The amino acids were from ICN Biomedicals (Aurora, Ohio), and the peptides were from Sigma-Aldrich (St. Louis, Mo.). Each analyte was individually diluted in pH 9.2, 10 mM carbonate buffer, which was passed through a 0.2 µm filter (Pall, East Hills, N.Y.) prior to use. The amino acids and peptides in each solution were labeled fluorescently using fluorescein-5-isothiocyanate (FITC; Molecular Probes, Eugene, Oreg.).[34] For amino acids, 200 µL of 6 mM FITC in dimethylsulfoxide (DMSO) were combined with 600 µL of a 3 mM solution of each amino acid. For peptides, 200 µL of a 2 mM solution of each peptide were combined with 50 µL of 6 mM FITC in DMSO. All solutions were allowed to react at room temperature in the dark for at least 24 h; longer times (up to 5 days) enabled the reaction to go to completion such that the unreacted FITC peak was eliminated.

Prior to use, microchip channels were filled with 10 mM carbonate buffer, pH 9.2, having 0.5% (w/v) hydroxypropyl cellulose (HPC; average MW: 100,000; Sigma-Aldrich). The HPC served to minimize electroosmotic flow (EOF) and analyte adsorption to the channel walls.[35-37] Channels were filled by micropipetting 16 µL of the buffer into reservoirs 1, 2, and 3 (FIG. 3) and applying vacuum to reservoir 4, after which reservoir 4 was also filled with 16 µL of buffer. To load samples in the injection well (reservoir 1) when HPC-containing buffer was used as run buffer, vacuum was applied to reservoir 1 to remove its contents, and the well was filled with 16 of amino acid or peptide sample in 10 mM carbonate, pH 9.2. To run a separation without HPC in the buffer, the HPC-containing buffer was vacuumed from the device; the channels and reservoirs 2-4 were filled with pH 9.2, 10 mM carbonate buffer; and reservoir 1 was filled with 16 µL of sample. For injection, reservoirs 1, 2, and 4 (FIG. 3) were grounded, and reservoir 3 was maintained at an injection voltage ranging from +300 V to +1250 V (depending on the separation voltage used) for at least 20 s. During separation, reservoirs 1 and 3 were held at the injection voltage, reservoir 2 was grounded, and a potential between +1.0 and +4.5 kV was applied at reservoir 4. All peaks were identified by spiking.

The laser-induced fluorescence system has been described previously.[33] Briefly, excitation of the fluorescently labeled amino acids and peptides was achieved with the 488 nm line from an air-cooled Ar ion laser, which was focused ~500 µm from the end of the separation channel using a 20×, 0.45 NA objective. Fluorescence was collected with the same objective, and stray light was removed by confocal spatial filtering with a 200-µm-diameter pinhole. A photomultiplier tube detected photons passing through the pinhole, and the detector output was recorded on a computer at 100 Hz.

Safety Information

The 40% aqueous KOH and 10% buffered HF used as etchants to micromachine the Si templates are both corrosive. To avoid skin or eye contact with these solutions, safety goggles, a face shield, and elbow-length nitrile gloves should be worn. The voltages used for electrophoretic injection and separation can cause electric shock, so appropriate precautions such as current-limiting settings on power supplies and isolation of electrical leads should be taken. Solvents for bonding PMMA and dissolving paraffin should be used in a fume hood. The high pressures used to test bond strengths pose a projectile hazard. A face shield should be worn, and the bonded substrates should be secured inside a metal container during testing.

Results and Discussion

Figure 4:
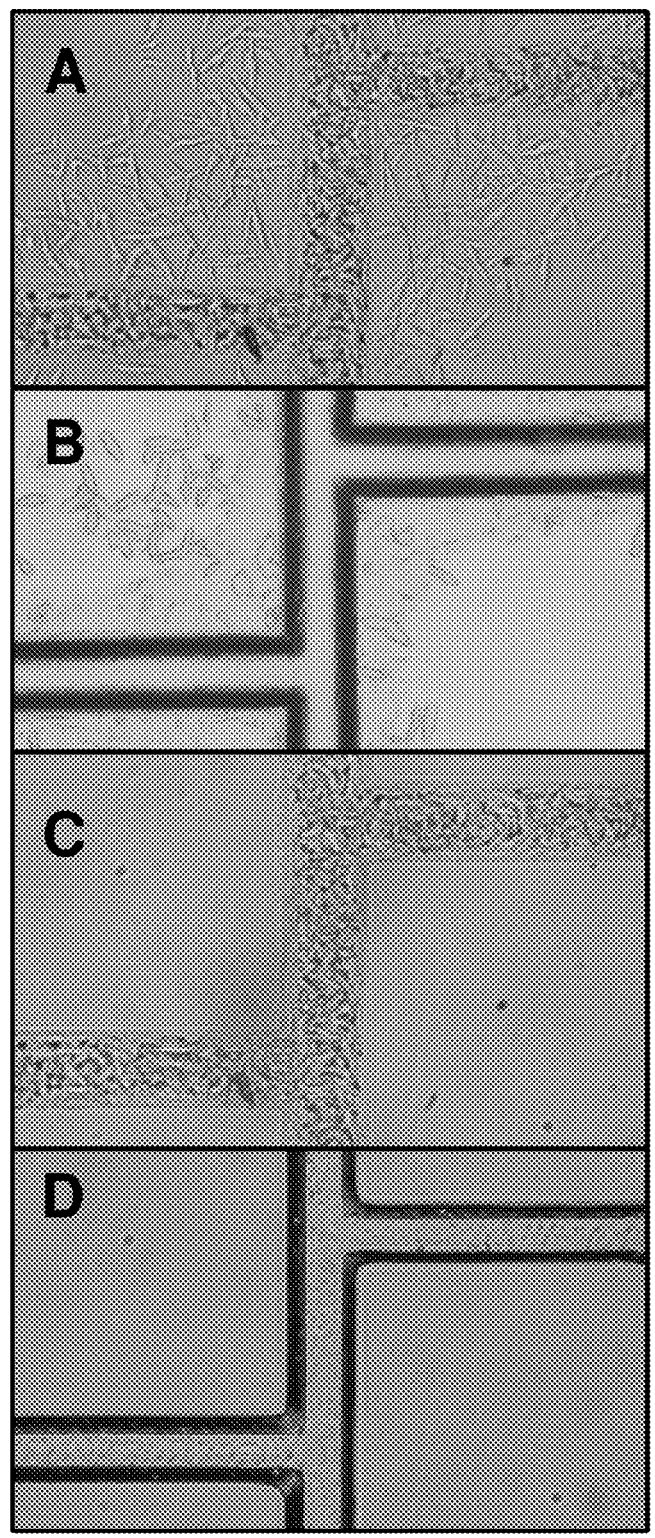
FIG. 4 shows photomicrographs of the double-T injector region of a device:
(A) PMMA/PDMS assembly just after filling the channels with sacrificial material; some paraffin wax had solidified outside the channels.
(B) A poorly defined microchannel resulting from solvent bonding without removing excess wax.

Reference is now made to FIG. 4. After filling the microchannels with the sacrificial material (see FIG. 2 and description above), it was sometimes observed that a small amount of paraffin wax had solidified outside of the imprinted channels (FIG. 4A). This was likely due to the hydrophobic interaction between the paraffin wax and the PDMS, and bonded devices made directly from these substrates typically had poorly defined channels (FIG. 4B) that led to reduced separation efficiency. This problem was largely eliminated by having the liquid sacrificial material in contact with PDMS for as little time as possible (removing substrates from the heating block 1-2 s after first introducing the liquid paraffin wax). Furthermore, residual paraffin wax outside the channel regions dissolved[38] into the PDMS within 1-2 h, leaving well-defined channels filled with the sacrificial material. FIG. 4C shows the same channel region presented in FIG. 4A, after 80 min in contact with the PDMS; essentially all the undesired sacrificial material had dissolved in the PDMS. Alternatively, the accumulation of sacrificial material outside of the channels could likely be eliminated by employing a less hydrophobic sealing material than native PDMS, such as $O_2$-plasma-oxidized PDMS.[6] FIG. 4D shows the channel intersection region of a solvent-bonded CE microchip made from the imprinted substrate from FIGS. 4A and 4C. The small amount of topography visible in the channels, caused by the granularity of the solidified wax, did not affect performance, as CE separations in such devices had symmetric peaks with reproducible theoretical plate counts.

FIG. 5 shows cross-sections of patterned features at various stages of microchip fabrication. A small indentation in the top of the sacrificial material, which is caused by paraffin shrinkage upon solidification, is visible in FIG. 5B. Profilometry indicates that the magnitude of shrinkage is less than ~10% of the channel cross-sectional area; these smaller dimensions are retained in the final bonded devices (FIG. 5C). Additionally, if the PDMS is left in contact with the wax-filled substrate at room temperature, wax from the channel dissolves into the PDMS at a rate of ~1 μm/h. Importantly, there has not been observed the total collapse of channel features during solvent bonding; such channel deformation occurs more commonly when thermally bonding polymers. It has been also found that the phase-changing sacrificial material and solvent bonding approach are successful with much shallower, 7-μm-deep channels.

Our comparison of the bond strength in thermally and solvent-bonded substrates yielded the following results. For solvent-bonded PMMA, all three test devices withstood the maximum tank pressure (2250 psi) without separating. In contrast, three thermally bonded PMMA devices failed at 145, 232, and 222 psi, giving an average failure pressure of ~200 psi. These tests show that solvent-bonded PMMA can withstand at least an order of magnitude higher internal pressure than thermally bonded PMMA. The ability to withstand pressures >200 psi is valuable for the replacement of viscous sieving media[39] commonly used in capillary gel electrophoresis of DNA and proteins.

The solvent-bonded microchips were tested by separating a mixture of amino acids at different applied voltages to find the range that provided the highest theoretical plate numbers. FIG. 6 shows the separation of FITC-labeled glycine, asparagine, phenylalanine and arginine at potentials ranging from 1.0 kV-4.5 kV. At 4.5 kV the four peaks are baseline resolved, and the separation is completed in just 8 s. The highest theoretical plate numbers were obtained between 2.5-3.5 kV, as shown in FIG. 7. The plateauing of theoretical plate numbers and their eventual decrease at higher potentials may be largely due to the 280-μm offset (center-to-center) in the double-T injector rather than Joule heating or other fundamental limits. For example, the width at half height of the glycine peak in the 4.5 kV separation in FIG. 6 is only 320 μm, making the injected sample plug length the most significant contributor to peak breadth.

To minimize electroosmotic flow and prevent analyte adsorption,[35-37] the channels were filled with buffer containing 0.5% (w/v) HPC prior to each run. In some cases, the run buffer also contained 0.5% HPC (e.g. FIG. 6). The migration time reproducibility for CE in HPC-free buffer was evaluated by running ten replicate injections of the amino acid mixture at 1 min intervals. The migration time for FITC-Arg had a relative standard deviation (RSD) of 0.9% for 10 consecutive runs, indicating that the adsorbed polymer coating was stable over that time. Furthermore, over two days with the channels flushed and refilled multiple times, the RSD was 1.5% for 25 runs. A representative separation performed in a channel that was treated with HPC, but filled with HPC-free buffer, is shown in FIG. 8. For comparison, a separation of the same mixture run in HPC-containing buffer is also shown. Theoretical plate numbers were not significantly different for the separations in the two solutions, but the selectivity changed slightly for some analytes, most likely due to increased buffer viscosity when HPC was present. For this reason, FITC-Asn and FITC-Phe were fully resolved when HPC was added to the run buffer (FIG. 8A), but not when HPC was absent (FIG. 8B). Passivating channel walls with an additive and then running the separation without that additive present in the run buffer should be useful where such buffer components would interfere with detection (e.g. mass spectrometry).

To further demonstrate the suitability of solvent-bonded CE microchips for high-performance biological analyses, FITC-labeled peptides were separated in HPC-containing buffer (FIG. 9). The separation performance was similar for the peptides and amino acids; peak a in FIG. 9 has a theoretical plate number of 43,000, corresponding to $1.7 \times 10^6$ plates/m. Peptides in buffer lacking HPC (not shown) were also separated, and the plate numbers and resolution were similar to those in FIG. 9.

The excellent performance of these PMMA microchips in CE clearly demonstrates the usefulness of the solvent bonding technique. Electric fields nearly twice as high as those previously reported were applied in PMMA microchips,[40] which enabled separations with >40,000 theoretical plates in ~10 s. It is believed that higher fields are possible in the devices of the present invention because the robust bonding is more resistant to dielectric breakdown at elevated voltages. Furthermore, a single device was used for >300 separations over the course of 3 months with no degradation of separation performance. These results demonstrate a significant advance in fabrication technology that should make polymer substrates more attractive for a broad range of microchip analyses.

A key advantage of the phase-changing sacrificial material, solvent bonding approach is that it should be generalizable to other combinations of polymeric substrates, sacrificial materials, and bonding solvents. The requirements for application to new systems are (1) a sacrificial material that has a melting temperature below the glass transition temperature of the chosen polymer, and (2) a bonding solvent that can dissolve the polymer substrate but not the sacrificial material.

Conclusion and Summary of Example I

It has been shown that polymeric microchips can be created by using a sacrificial material to protect channel integrity during solvent bonding. This phase-changing sacrificial material fabrication method is simple to implement, and tests show that solvent-bonded devices can withstand >10-fold higher internal pressures than thermally bonded substrates. CE separations of FITC-labeled amino acids and peptides were successfully carried out on solvent-bonded devices in as little as 8 and 15 s, respectively, with theoretical plate numbers exceeding 40,000 for both analyses. Finally, devices can be operated at electric fields >1500 V/cm and can be used for hundreds of electrophoretic separations without any change in performance. Solvent bonding with phase-changing sacrificial materials should help to overcome some of the previous limitations of polymer microfluidic devices and make them more attractive for chemical analyses.

Example II

Imprinting

Thermal Imprinting

CE channels were fabricated into the devices by using a photolithographically patterned and anisotropically etched silicon template to imprint a channel design into a polymer piece (FIG. 10). In general, this is done by sandwiching the silicon template and polymer substrate together and warming both to a temperature above the glass transition point of the polymer to create channels in PMMA.

To imprint PC, 1.75"×1"×1/8" substrates (HYZOD Polycarbonate, Sheffield Plastics, Sheffield, Mass.) were paired with silicon templates and secured between glass microscope slides and aluminum blocks by three 2-in. C-clamps to prevent accidental slippage of any of the pieces. The entire assembly was placed in a convection oven at 174° C. and softened for 10 minutes. Next the apparatus was removed from the oven and the C-clamps were tightened approximately 1/8 of a turn, after which the assembly was returned to the oven. A similar tightening was performed after one hour. After a total imprinting time of ninety minutes, the device was removed from the oven, the clamps were loosened, and the substrate was released from the template. PETg channels were constructed in a similar fashion with oven temperatures of 120° C. Imprinted substrates were cleaned with soap and water and examined under an optical microscope.

Solvent Imprinting

To avoid the high temperatures and lengthy imprinting times needed for thermal imprinting in sturdier polymers, solvent imprinting was explored. Imprinting of PMMA, PC, and PETg pieces (1/8" thickness) was tested in combination with acetonitrile, acetone, or methylene chloride as the solvent. One side of the polymer piece was reversibly sealed to PDMS to prevent inadvertent contact with the solvent. 600 μL of solvent was pipetted onto the opposite face of the substrate and allowed to stand for 30 seconds. The polymer piece and a silicon template were slowly brought together at an angle, allowing air bubbles to escape out the side. The assembly was sandwiched between metal blocks and clamped in a vice in a manner similar to FIG. 10. After the substrate was imprinted, excess solvent was removed with vacuum, and a razor blade was used to gently lift the polymer away from the template. Solvent-imprinted channels were then cleaned with soap and water and compared to those that were thermally imprinted in the same material. The channel pattern embossed into both thermally and solvent-imprinted substrates is shown in FIG. 11.

Sacrificial Material

After imprinting and cleaning, the polymer substrate was sealed to a clean, flat, 1/16" thick piece of PDMS, enclosing the channels. 3-mm-diameter holes in the PDMS were aligned with the imprinted channel ends. The polymer/PDMS assembly was warmed for 30 sec on a heating block at 70° C. for all sacrificial materials except eicosane (45° C.) or polyethylene glycol (PEG) 400 (no heating), and a pipet was used to quickly transfer melted sacrificial material from a heated vial to three of the access holes (see FIG. 11). Vacuum was used at the fourth reservoir to assist in filling the channels and removing bubbles. Next, the assembly was removed from the heating block and allowed to cool to room temperature; for PEG 400 the device was placed on ice to solidify the sacrificial material. After the sacrificial material had solidified, the assembly was inspected under a microscope. If small amounts of wax sacrificial material had solidified outside the channel, the entire assembly was warmed on a 45° C. heating block for 2.5 minutes to dissolve the extraneous wax in PDMS. Lastly, the PDMS was removed from the cooled devices. Table 5 lists the tested sacrificial materials and their melting points.

TABLE 5

Sacrificial materials and melting points.[63-67]

| Sacrificial Material | Melting Point (° C.) |
|---|---|
| Paraffin wax (Service Assets, Newport Beach, CA) | 50-57 |
| PEG 3350 | 52-56 |
| PEG 1450 | 44-48 |
| PEG 400 | 17-19 |
| Eicosane | 37 |
| Lauric acid | 44 |
| Solid vegetable oil (Crisco Shortening, J. M. Smucker Co., Orville, OH) | 45 |
| Soy wax + | 57 |
| Crème wax + | 52 |
| + from Yaley Enterprises, Redding, CA 96002 | |

Solvent Bonding

Solvents were tested both for their ability to bond the polymer substrates, as well as for their ability to dissolve one of the sacrificial materials (Crème Wax). Chemical resistance charts were consulted, and only solvents for which PC or PETg were reported as demonstrating poor resistance were evaluated.[68] Relative polarity of the solvents was also considered. Because most of the sacrificial materials had low polarity, solvents with high relative polarity were preferred; relative polarity values are included in the Table 7.

To test the solubility of Crème wax, 7 mL of solvent was added to 5-6 mg of Crème wax in a small vial and agitated. Observations of the resulting mixture were recorded initially, as well as after 5 min, 10 min, 30 min, and 24 hours. Cyclohexane, a good solvent for waxes, was included as a control.

To test for bonding, 100 μL of solvent was pipetted onto 1/2"×1/2"×1/8" squares of PC or PETg. The substrate was then slowly combined with a second piece of polymer and held together for 2 minutes with moderate pressure. If bonding was incomplete after 2 minutes, the pieces were held together an additional 10 minutes.

To prepare CE microchips, 400 μL of solvent were pipetted directly onto the surface containing the wax-protected channels. PDMS pieces were sealed to the nonbonding sides of the polymer to protect the device exterior. Then the two pieces were brought in contact and held together with ~2 psi until bonding was complete. After bonding, the pressure was released and the PDMS was detached from the device. To remove the sacrificial material, 10-20 μL of cyclohexane was pipetted into the access holes above the channels and the device was warmed until the sacrificial material melted. Vacuum was applied to each of the reservoirs to remove the melted wax, after which the channel was refilled with fresh cyclohexane to dissolve any residual wax. Finally, the device was cooled to room temperature and examined microscopically for completeness of wax removal.

Microchip CE Analysis

Initial analysis was performed on thermally imprinted and solvent-bonded PC and PETg devices. Prior to microchip use, 20 µL of 100 mM Tris buffer (pH 8.1) with 0.5% hydroxypropyl cellulose (HPC) were pipetted into reservoirs 1, 2, and 3, and vacuum was applied at reservoir 4 to fill the channels (FIG. 11). The HPC reduces the electroosmotic flow and analyte adsorption to the channel walls.[69] The filled channels were examined under a microscope for the absence of trapped air, and 20 µL of buffer were added to reservoir 4. To load sample in the injection well, reservoir 3 was emptied, and then filled with 10-20 µL of analyte. Fluorescein (40 µM in Tris buffer) was the test analyte in both PC and PETg devices to evaluate injection and detection. A mixture of the peptides FLEEI, Leu Enkephalin, and GGYR was also used to evaluate the separation capabilities of a PC device. To effect injection, reservoirs 2, 3, and 4 were grounded while +800 V were applied at reservoir 1 for 30 sec, driving the sample through the intersection toward reservoir 1 (see FIG. 11). To inject a plug of sample into the separation channel, reservoir 2 remained grounded while reservoirs 1 and 3 were held at the injection voltage and +1250 V were applied at reservoir 4.

The separated fluorescent analytes were excited using the 488-nm line from an air-cooled Ar ion laser focused in the separation channel ~50 mm from the injection region. A 20×0.45 NA objective focused the laser and collected fluorescence, while a 200 µm confocal pinhole was used to remove stray light. A photomultiplier tube detected photons passing through the pinhole, and the detector output was recorded on a computer.

Results and Discussion

Thermal Imprinting

Using a microscope, it was observed that in PC, the smaller side channels tended to shift during thermal imprinting (FIG. 12, left). While this is also seen occasionally with PMMA (<30% of the time) shifting occurred without exception for PC substrates that were thermally imprinted, cooled to room temperature, and released. The distortion seems to occur because of uneven cooling in the polymer. The issue was resolved by cooling the imprinted assembly to 145° C. (5° below the glass transition temperature) and then immediately releasing the substrate from the template (FIG. 12, right). No channel shifting was observed in PETg (FIG. 13). Table 6 summarizes the results of the optimization of imprinting temperatures for PC and PETg.

TABLE 6

Thermal imprinting temperatures and conditions.

| Polymer | Temperature (° C.) | Result |
|---|---|---|
| PC | 155 (up to 2 hours) | Underimprinted |
|  | 165 (up to 2 hours) | Underimprinted |
|  | 174 (1 hour 15 min) | Ideal |
|  | 180 (1 hour 15 min) | Slight bubbling |
|  | 200 (45 min) | Moderate bubbling |
|  | 210 (45 min) | Extreme bubbling |
| PETg | 120 (20 min) | Slightly Underimprinted |
|  | 120 (30 min) | Ideal |

Solvent Imprinting

Acetonitrile, with pressure applied for 2-5 minutes, produced the best solvent-imprinted PC and PMMA channels. Acetone, with pressure applied for 5-10 minutes, proved the most useful in imprinting PETg. Acetonitrile-imprinted PETg tended to develop irregular features in the corners between channels. Combinations of these two solvents did not offer any advantages relative to the single components. FIG. 14 shows solvent-imprinted channels made in all three polymers.

Solvent-imprinted PETg required several minutes to achieve structural integrity after removal from the template. Over-tightening the bench-mounted vice to apply pressure during solvent imprinting increased polymer cracking, especially for PC. Solvent-imprinted devices made of any of the three polymers could be filled with wax sacrificial materials as easily as their thermally imprinted counterparts, although channels greater than 30 µm deep filled most easily.

For PC devices, crazing was sometimes observed when solvent imprinting was coupled with solvent bonding (FIG. 15). Crazing occurs in polymers when an organic fluid is preferentially absorbed at sites under high dilational stress, such as defects and cracks; processing and assembly also increase strain, affecting the incidence of crazing.[70] Carefully sanding the substrate edges and annealing both top cover and bottom substrate pieces at 175° C. for 1 hour, followed by slowly cooling back to room temperature minimized cracking, but did not completely eliminate it (see FIG. 15). PETg and PMMA did not show significant evidence of crazing.

Sacrificial Material

Waxes were the most effective sacrificial materials that were tested in this experiment. They were generally resistant to polar solvents such as acetonitrile, could be removed easily using hexanes without damaging the polymer substrates, and tended to have convenient melting points just above room temperature for phase-changing sacrificial operations. The PEG materials had the disadvantage of requiring a different solvent system from the waxes. Also, working with PEG 400, a liquid at room temperature, required maintaining the device temperature below 15° C. to solidify the sacrificial material during bonding and generally produced lower-quality channels. Viscosity and solubility were issues with lauric acid and eicosane, while vegetable oil soy wax disrupted the PDMS to polymer seal during filling. Crème wax and paraffin wax offered similar advantages in terms of viscosity, solubility, and convenience. As paraffin wax solidified, the surface became slightly uneven, which was reflected in the final channel (FIG. 16A). Crème wax channels were appreciably smoother (FIG. 16B), which should provide improved separation performance.

Solvent Bonding

Table 7 summarizes the results of testing different solvents for bonding and Crème Wax solubility properties. Of the solvents evaluated, acetone and acetonitrile were the most appropriate for this application. In practice, acetonitrile-bonded devices seemed to seal more evenly and demonstrate less solvent/sacrificial material interaction than acetone-bonded devices.

Extricating the sacrificial material after solvent bonding was a challenging aspect of this project. Sometimes when the sacrificial material was removed, residual solvent in the polymer caused the still-softened channels to collapse and become blocked irreversibly.

TABLE 7

Comparison of solvents for bonding and Crème Wax solubility properties.

| | | Crème Wax Solubility* | | | | Bonding | |
|---|---|---|---|---|---|---|---|
| Solvent | Relative Polarity[71] | Initial | 5 min | 10 min | 30 min | 24 hr | 2 min | 10 min |
| Cyclohexane (control) | 0.006 | sls | Ss | cs | Cs | cs | Poor | Poor |
| Acetone | 0.355 | ns | Sls | sls | Sls | ss | Good | Good |
| Acetonitrile | 0.460 | ns | Sls | sls | Sls | ss | Good | Good |
| DMSO | 0.444 | ns | Sls | sls | Sls | sls | Fair | Fair |
| Ethylene glycol | 0.790 | ns | Ns | ns | Ns | ns | Poor | Poor |
| Methylene chloride | 0.309 | ns | Sls | sls | Ss | cs | Fair | Good |

TABLE 7-continued

Comparison of solvents for bonding and Crème Wax solubility properties.

| Solvent | Relative Polarity[71] | Crème Wax Solubility* | | | | Bonding | |
| --- | --- | --- | --- | --- | --- | --- | --- |
| | | Initial | 5 min | 10 min | 30 min | 24 hr | 2 min | 10 min |
| NaOH (10%) | NA | ns | Ns | ns | Ns | ns | Poor | Poor |
| Phenyl acetate | NA | ns | Sls | sls | Sls | sls | Fair | Fair |

*Degree to which a sample of Crème wax dissolved.
Abbreviations: ns = not solubilized, sls = slightly solubilized, ss = significantly solubilized, cs = completely solubilized.

Allowing the solvent to evaporate for several minutes after bonding and before removing the sacrificial material helped minimize channel collapse, especially with PETg. In bonded PETg devices the melted sacrificial material could be evacuated relatively easily. Conversely, much more difficulty was encountered in removing the sacrificial material from PC channels, perhaps because of its hydrophobicity being greater than PETg or PMMA. In addition, air pockets were sometimes observed when PC channels were filled with aqueous solutions. Generally, solvent-imprinted devices were more difficult to clear of sacrificial material than thermally imprinted ones. Diluting the bonding solvent with water to decrease solvation did not overcome this issue and weakened the overall bond strength. FIG. 17 contains photographs of completed PETg and PC solvent-bonded devices.

Microchip CE Analysis

Initial results using the PC and PETg devices for chemical analysis were promising. Injections and CE of fluorescein were achieved using both PETg and PC devices. FIG. 18 shows fluorescein being loaded through the injection region of a thermally imprinted PETg device. FIG. 19 shows the detection of injected fluorescein in a thermally imprinted PC device. A CE separation of three analytes on a PC device was also achieved as shown in FIG. 20. These analyses are encouraging evidence that solvent-bonded devices in PC and PETg will be viable tools for CE.

Conclusions and Summary of Example II

Solvent bonding of PC and PETg has been demonstrated as a realistic option for fabrication of CE microchips. Thermal imprinting techniques for these two polymers were developed, and solvent embossing was explored as an alternative. Different bonding solvents and phase-changing sacrificial materials were also evaluated, and the best results were obtained with acetonitrile as the solvent and Crème wax as the sacrificial material. Finally, simple CE separations were performed on completed devices to assess their potential for microchip chemical analysis applications. The fabrication techniques developed and implemented here have the potential to both simplify and improve microdevice construction.

Example III

Sample Preparation and Materials

All buffer solutions were made using purified water from a Barnstead EasyPure UV/UF system (Dubuque, Iowa) and passed through a 0.2-μm filter (Pall, East Hills, N.Y.) prior to use. Peptide standards (Sigma-Aldrich, St. Louis, Mo.) were labeled fluorescently[99] by combining 200 μL of a 2 mM solution of each peptide in 10 mM, pH 9.2 carbonate buffer with 50 μL of 6 mM fluorescein isothiocyanate (FITC; Molecular Probes, Eugene, Oreg.) in dimethylsulfoxide. The mixture was allowed to react at room temperature in the dark for at least three days prior to use. R-phycoerythrin (R-PE; Polysciences, Warrington, Pa.) and recombinant enhanced green fluorescent protein (GFP; Clontech, Palo Alto, Calif.) were used after dilution in run buffer. Diluted R-PE solutions for the calibration curve, ranging in concentration from 40 ng/mL to 500 μg/mL, were prepared in 20 mM, pH 8.0 Tris buffer.

The in situ-polymerized semipermiable membranes for EFGF and protein preconcentration microdevices were similar to those employed for capillary-based EFGF.[95] The prepolymer solution consisted of 34 wt % hydroxyethylmethacrylate, 24 wt % methylmethacrylate, 17 wt % 100 mM Tris buffer (pH 8.1), 21 wt % poly(ethylene glycol) acrylate, 3 wt % ethylene glycol dimethacrylate, and 1 wt % 2,2-dimethoxy-2-phenylacetophenone (photoinitiator). All reagents for the semipermiable membranes were obtained from Sigma-Aldrich and used as received. The PMMA for device substrates was Acrylite OP-3 (Cyro, Rockaway, N.J.), and the paraffin wax PCSM (melting point: 65° C.) was from Service Assets (Newport Beach, Calif.).

Microdevice Fabrication

Reference is now made to FIG. 21. Silicon wafers were patterned photolithographically and wet etched; these substrates served as templates for hot embossing PMMA as described in an earlier report.[100] FIG. 21 illustrates the different device fabrication steps for interfacing a semipermiable membrane with microchannels. In brief, this procedure involves filling a microchannel with PCSM, placing a PMMA piece with an opening on top of the imprinted substrate, filling the well with prepolymer solution, UV photopolymerization, and then PCSM melting and removal.

EFGF Microdevices.

Reference is now also made to FIG. 22. The imprinted PMMA had straight microchannels that were 3 cm long (FIG. 22) with trapezoidal cross-sections that were 30 μm deep, having a width that increased from 40 to 80 μm from bottom to top. A flat, 2-mm-thick piece of poly(dimethylsiloxane) (PDMS; Sylgard 184, Dow Corning, Midland, Mich.) had two 500-μm-diameter through holes set 3 cm apart. The PDMS was sealed reversibly as a cover layer to the imprinted PMMA piece (FIG. 21A) such that the drilled holes aligned with the channel ends. The temperature of the PDMS/PMMA assembly was raised to 85° C. on a heating block, and 10 μL of melted paraffin wax PCSM were transferred quickly from a heated vial to one of the holes in the PDMS piece. Vacuum was applied to the other opening to fill the channel with melted PCSM (FIG. 21B). The assembly was transferred to a heating block at 35° C. for 3 min to solidify the PCSM (FIG. 21C), and then the system was cooled to room temperature. Lowering the device temperature in two steps prevented the deposition of solid PCSM in regions beyond the microchannels.[98] Next, the PDMS was peeled from the surface, and a PMMA cover plate having a region of changing CSA cut from its center with a $CO_2$ laser cutter (C-200, Universal Laser Systems, Scottsdale, Ariz.) was aligned with the imprinted, PCSM-protected PMMA as shown in FIG. 21C and FIG. 22 (left). In addition to the changing CSA pattern, rectangular buffer reservoirs and a 0.9-mm-diameter hole for connecting tubing to provide counterflow were cut from the PMMA cover plate (see FIG. 22). The substrates were clamped together, and epoxy (No. 14250, Devcon, Danvers, Mass.) was applied around the perimeter of the assembly. Four holes, one at each of the device corners, were drilled through the cover plate to allow air pockets to escape when the prepolymer solution was added. Melted paraffin wax was pipetted and then solidified in the pump access hole and the high-field reservoir, and rectangular PDMS plugs were inserted into the low-field reservoirs (FIG. 22). Approximately 400 μL of prepolymer solution were pipetted into the changing CSA region (FIG. 21D), also filling the interstitial space between the two PMMA substrates. The prepolymer-containing device was mounted on a copper block maintained at 4° C. and placed under a 320 W Hg arc lamp (Model 5000, Dymax, Torrington, Conn.) for 5 min to polymerize the material of the semipermiable membrane (FIG. 21E). Cooling during polymerization prevented the PCSM from melting. Next, the device was heated to 85° C. to liquefy the PCSM, which was removed from the channel and reservoirs by applying vacuum (FIG. 21F). Once the EFGF microchip had returned to room temperature the channels were flushed with hexanes (EM Science, Darmstadt, Germany) to dissolve residual PCSM, and the PDMS plugs that defined the low-field buffer reservoirs were removed. Finally, a 20-cm-long piece of flexible tubing (0.9 mm O.D.) was inserted into the pump access hole and sealed in place with epoxy (FIG. 22, right). A photomicrograph of a completed EFGF microchannel is presented in FIG. 21G, and an image of an entire μ-EFGF device is shown in FIG. 22, right.

Microchip Preconcentration Systems

Reference is now made to FIG. 23. Imprinted PMMA microchannels had the same dimensions as those in EFGF microdevices and were filled with PCSM as described above. A PMMA cover plate, which had two 3-mm-diameter through holes set 3 cm apart and one 5-mm-diameter opening centered between the two smaller holes, was aligned with the PCSM-filled PMMA bottom piece (FIG. 23). The two PMMA substrates were clamped together, and the two smaller holes were filled with PCSM. Then, 200 μL of prepolymer solution were added to the membrane reservoir. Photopolymerization and PCSM removal were carried out as described above for EFGF microchip fabrication.

EFGF Microdevice Operation

A 100 μL gas-tight syringe (Hamilton, Reno, Nev.) having run buffer of either 20 or 100 mM Tris (pH 8.1) with 0.5% w/v hydroxypropyl cellulose (HPC) was connected to the flexible tubing and placed in a syringe pump (PHD 2000, Harvard Apparatus, Holliston, Mass.), enabling counterflow as low as 0.4 nL/min in the channel. Two Pt electrodes were connected to a high-voltage power supply and inserted into the low-field reservoirs, which were filled with run buffer, and a grounded Pt electrode was placed in the high-field reservoir (FIG. 22). For analyte introduction the counterflow was stopped, and the high-field reservoir was filled with sample dissolved in buffer. The mixture was injected electrokinetically for 30 s at 500 V, after which the power supply was turned off. Modifying the injection time or voltage would accommodate a range of sample concentrations or analyte electrophoretic mobilities. After injection the sample was pipetted from the high-field reservoir, and the well was rinsed and refilled with run buffer. The applied potential and counterflow were then adjusted to focus the proteins or peptides into discrete bands.

Microchip Capillary Electrophoresis.

CE experiments were performed in solvent-bonded PMMA microchips. Device fabrication, channel dimensions, and operating procedures have been described previously.[98] The separation distance was 2.5 cm, and the channel cross-sectional dimensions were the same as for EFGF microchips. The run buffer was 100 mM Tris (pH 8.1) with 0.5% w/v HPC, the injection potential was +300 V, and the separation potential was +1.0 kV.

Protein Preconcentration Microchip Operation.

Reference is again made to FIG. 23. To concentrate proteins the microchannel was filled with 20 mM Tris pH 8.0 buffer containing 0.5% HPC; buffer was placed in the buffer and membrane reservoirs, and R-PE solution was loaded in the sample reservoir (see FIG. 23B). R-PE was concentrated at the semipermiable membrane when 500 V were applied between the sample and membrane reservoirs.

Fluorescence Instrumentation

Detection of focused analytes in μ-EFGF devices was accomplished as described previously.[95] Briefly, micrographs were obtained by passing the 488 nm line of an Ar ion laser into a 4×, 0.12 N.A. objective on an inverted microscope (TE300, Nikon, Tokyo, Japan) and imaging the resulting fluorescence with a digital camera (Coolpix 995, Nikon). Photomicrographs were converted to electropherograms by averaging the fluorescence intensity across the channel at each point along the focusing column using the image processing program ImageJ 1.34s (National Institutes of Health, USA). Noise due to laser speckle and reflections from the membrane was filtered from the electropherograms by boxcar averaging. When all focused bands could not be probed in a single image, the column was scanned through a confocal detection point using a translation stage. For scanning detection the laser was passed through a 10× beam expander prior to being focused with a 20×, 0.45 N.A. objective. The collected fluorescence was filtered spatially with a 200-μm-diameter pinhole and detected at a photomultiplier tube (HC 120-05, Hamamatsu, Bridgewater, N.J.).

For microchip preconcentration experiments the digital camera was replaced with a cooled CCD camera (CoolSnapHQ, Roper Scientific, Tucson, Ariz.). A 200 ms exposure time was selected, and the average intensity in the channel was determined for each CCD image. A calibration curve was generated from the average fluorescence signals of standard R-PE solutions flowing through the channel. The R-PE concentration factor at the membrane was obtained from the fluorescence signal and the calibration curve.

Results and Discussion

For the PCSM approach to be effective for in situ membrane incorporation, the solid sacrificial material must not be soluble in either the monomer solution or the polymerized hydrogel. The prepolymer used in these studies could be placed in contact with solid paraffin wax in a microchannel for >20 min without any observable dissolution taking place at the microscopic level. In contrast another potential PCSM, poly(ethylene glycol), dissolved readily in the monomer mixture and was not suitable. While paraffin wax and the semipermiable membrane used here made an appropriate combination in this example, other PCSMs are contemplated for interfacing different materials for the semipermiable membrane with microchannels.

Initial experiments that applied solvent bonding[98] to affix the PMMA substrates together prior to adding the prepolymer solution frequently resulted in air pockets forming at the PMMA-membrane junction at the low-field end of the EFGF microchips. While these bubbles did not form in every device, the fabrication yield was sufficiently low that alternatives were pursued. It was found that when the semipermiable membrane served both as the ionically conductive membrane to provide the electric field gradient and as the adhesive to bond the cover plate to the patterned substrate, air pockets were not observed at the PMMA-membrane junction. In this design the thin semipermiable membrane layer extending beyond the changing CSA region made current leakage a possible concern. However, the semipermiable membrane thickness in the adhesive region (<10 μm) was much less than in the electric field gradient formation area (>1 mm), and the semipermiable membrane was ~100 times less conductive than the run buffer solution in the channel.[95] As such, problems with current leakage in semipermiable membrane-bonded devices were not observed.

Reference is now made to FIG. 24. FIG. 24A shows the separation of two natively fluorescent proteins, R-PE and GFP, in an EFGF microchip. These same species had been analyzed previously in a capillary-based EFGF device (FIG. 24B),[95] which allowed the performance to be compared. Average peak widths in the microchip separation were over fourfold narrower than those in the capillary-based device, and the resolution increased threefold. Although the comparison between the two platforms is not perfect because the buffer composition and run conditions differed somewhat, the decreased peak widths in the μ-EFGF experiment in the presence of an electric field gradient comparable to that in the capillary device (based on similar peak spacing) indicate that band broadening is reduced in μ-EFGF systems. This observation is consistent with the expectation that as channel cross-sectional dimensions shrink, Taylor dispersion decreases.[96]

Reference is now made to FIG. 25. With a lower applied voltage that created a shallower gradient in a μ-EFGF device, it was possible to focus a mixture of fluorescently labeled peptides that had electrophoretic mobilities spaced more closely than R-PE and GFP. For comparison the peptides were analyzed by μ-EFGF (FIG. 25A) and μ-CE (FIG. 25B) using the same initial concentrations and run buffer. Peak resolution calculations for the two analyses, provided in Table 8, indicate comparable separation for peak pairs (a-b) and (b-c). The resolution for peaks (c-d) was considerably higher in the μ-EFGF study, presumably due to a shallower electric field gradient near the high-field end of the device. While the buffer conductivity precluded the use of electric fields above ~300 V/cm in μ-CE, it has been shown that higher-resolution separations of these peptides are possible in 10 mM carbonate buffer with an electric field of 1,000 V/cm.[98] Importantly, the μ-EFGF experiments demonstrate an improvement in resolution over capillary-based EFGF as a result of decreased dispersion in the smaller channels, and the separation performance is comparable to μ-CE.

TABLE 8

Resolution between adjacent peaks for the separations shown in FIG. 25.

|  | a-b | B-c | c-d |
| --- | --- | --- | --- |
| μ-EFGF | 4.3 | 1.3 | 7.9 |
| μ-CE | 5.1 | 1.2 | 1.4 |

The ability of μ-EFGF to concentrate analytes is also evident in FIG. 25. The normalized, background-subtracted fluorescence signal for FITC-FLEEI was 6.2 for μ-EFGF and 0.04 for μ-CE, showing a concentration enhancement of >150-fold in μ-EFGF, which is especially notable given the <10 min total analysis time. In these experiments the gain in the signal-to-noise ratio was less than 150-fold, due to the higher noise levels in on-column scanning detection in μ-EFGF compared to stationary point detection in μ-CE. To reduce noise in the scanning setup, improved spatial filtering could be used to avoid detection of semipermiable membrane background fluorescence; alternatively, focused peaks could be eluted past a point detector.[94]

Reference is now made to FIG. 26. To quantify the enrichment factor in microchip membrane-based protein preconcentration, a calibration curve was generated from the fluorescence signal from flowing standard R-PE solutions (FIG. 26). Linear regression yielded a slope of 1.92, an intercept of 7.51 and an $R^2$ value of 0.9984. When 40 ng/mL R-PE was transported electrokinetically to accumulate at the membrane for 40 min, a CCD signal of 850 was obtained, corresponding to a concentration of 450 μg/mL (FIG. 26), a >10.000-fold enrichment factor. For higher-concentration R-PE samples, the fluorescence signal exceeded the range of the calibration curve after 30 min of loading. With shorter concentration times, significant enrichment factors were also achieved. For example, 100 ng/mL R-PE was concentrated ~4,000-fold in 15 min. These results illustrate the power of interfacing hydrogel membranes with microfluidics to preconcentrate samples.

Conclusions and Summary of Example III

A simple method for the in situ polymerization of semi-permeable membranes in microfluidic devices is shown in this example. Channels are first filled with a liquid, which becomes a protecting sacrificial material upon solidification. A monomer solution is then poured over the filled microchannels and UV polymerized to form an ion-permeable hydrogel. Finally, the PCSM is melted and removed, leaving a microfluidic network interfaced with a polymer membrane.

Application of this fabrication approach in making μ-EFGF devices and membrane-based protein preconcentration microchips was shown. Because the μ-EFGF channel cross-sectional dimensions were smaller than those of previous membrane-based EFGF setups, Taylor dispersion was reduced, resulting in narrower focused bands. EFGF of natively fluorescent proteins was demonstrated with improved resolution compared to earlier work. Moreover, fluorescently labeled peptides were focused with >150-fold sample enrichment and comparable resolution to μ-CE. Membrane-based protein preconcentration microchips were also shown to provide sample enrichment factors of >10,000, significantly increasing the potential concentration range of biological specimens that can be analyzed by μ-CE. Finally, this general fabrication approach should be adaptable to other applications that require an ion-permeable hydrogel to be interfaced with microchannel networks, and as such should provide a useful tool for the development of integrated microfluidic systems.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A method for forming capillaries in a substrate for a microfluidic device comprising:
    providing a substrate of a polymeric material;
    forming microchannels in a surface of the substrate;
    reversibly sealing a cover layer on the substrate surface over the microchannels enclosing the microchannels by the cover layer and the substrate;
    filling the enclosed microchannels with a liquid sacrificial material which becomes solid after the filling;
    removing the reversibly sealed cover layer from the substrate and microchannels filled with the solid sacrificial material;
    affixing a top cover over the filled microchannel by forming a semi-permeable membrane material in situ over the microchannels to form the top cover comprising a membrane of the membrane material;
    removing the sacrificial material from the microchannels to form microcapillaries free of the sacrificial material, the sacrificial material essentially non-reactive and non-soluble with the material of the substrate to the extent it does not bond with the material of the substrate, and the sacrificial material non-reactive with the semi-permeable membrane material and the substrate material to the extent it does not bond with or materially degrade the properties of or bonding of the membrane material, and the substrate.

2. The method of claim 1 wherein the forming of the semi-permeable membrane material in situ comprises applying a prepolymer solution over the microchannels filled with the sacrificial material, and polymerizing the prepolymer.

3. The method of claim 2 wherein the prepolymer comprises a photo-polymerizable material and a photoinitiator and the polymerizing the prepolymer comprises exposing the prepolymer to light to activate the photoinitiator.

4. The method of claim 1 wherein the filling of the enclosed microchannels with a liquid sacrificial material is accomplished by warming the sacrificial material to liquefy the sacrificial substance and applying the molten sacrificial substance to one or more first access holes to the microchannels, and applying a vacuum to a second access hole to the microchannels to cause the liquid to flow from the first access holes and fill the microchannels.

5. The method of claim 4 wherein the reversibly sealed cover layer is a siloxane.

6. The method of claim 1 wherein sacrificial material is liquefied and removed by heating to liquefy the sacrificial material where the sacrificial material has a melting point lower than the glass transition temperature of the polymeric material of the substrate and the material of the top cover.

7. The method of claim 1 wherein sacrificial material is liquefied and removed by applying a solvent that dissolves the sacrificial material.

8. A method for forming capillaries in a substrate for a microfluidic device comprising:
   providing a substrate of a polymeric material;
   forming microchannels in a surface of the substrate;
   reversibly sealing a cover layer on the substrate surface over the microchannels enclosing the microchannels by the cover layer and the substrate;
   filling the enclosed microchannels with a liquid sacrificial material which becomes solid after the filling;
   removing the reversibly sealed cover layer from the substrate and microchannels filled with the solid sacrificial material;
   affixing by solvent bonding a top cover over the filled microchannel,
the substrate and the top cover each of a different polymeric material and each having properties that allow solvent bonding by bonding solvent of the substrate and the top piece;
   removing the sacrificial material from the microchannels to form microcapillaries free of the sacrificial material, the sacrificial material essentially non-reactive and non-soluble with the material of the substrate to the extent it does not bond with the material of the substrate, and essentially non-reactive and non-soluble with the bonding solvent for the solvent bonding, to not materially degrade the material of or bonding of the substrate and top cover, or materially degrade the integrity of the microchannels.

9. The method of claim 8 wherein the filling of the enclosed microchannels with a liquid sacrificial material is accomplished by warming the sacrificial material to liquefy the sacrificial substance and applying the molten sacrificial substance to one or more first access holes to the microchannels, and applying a vacuum to a second access hole to the microchannels to cause the liquid to flow from the first access holes and fill the microchannels.

10. The method of claim 9 wherein the reversibly sealed cover layer is a siloxane.

11. The method of claim 10 wherein sacrificial material is liquefied and removed by heating to liquefy the sacrificial material where the sacrificial material has a melting point lower than the glass transition temperature of the polymeric material of the substrate and the material of the top cover.

12. The method of claim 8 wherein the reversibly sealed cover layer is a siloxane.

13. The method of claim 8 wherein sacrificial material is liquefied and removed by heating to liquefy the sacrificial material where the sacrificial material has a melting point lower than the glass transition temperature of the polymeric material of the substrate and the material of the top cover.

14. The method of claim 8 wherein sacrificial material is liquefied and removed by applying a solvent that dissolves the sacrificial material.

15. The method of claim 8 wherein the polymeric material of the substrate and the top cover are different and are comprised of poly(methyl methacrylate), or polycarbonate, or polyethylene terephthalate-glycol.

16. The method of claim 8 wherein the affixing of the top cover over the microchannels comprises:
   applying the bonding solvent upon the surface of the substrate with formed microchannels;
   applying a surface of the top cover upon the solvent covered surface under pressure conditions sufficient to solvent bond the surface of the top-cover to the substrate surface.

17. The method of claim 8 wherein the polymeric material of either or both the substrate and the top cover comprises a thermoplastic.

18. The method of claim 8 wherein the polymeric material of either or both the substrate and the top cover comprises poly(methyl methacrylate), or polycarbonate, or polyethylene terephthalate-glycol; the sacrificial material comprises paraffin wax, or soy wax, and the solvent applied upon the surface comprises acetonitrile, acetone, or phenyl acetate.

* * * * *